United States Patent
Stedman

(10) Patent No.: US 6,177,403 B1
(45) Date of Patent: Jan. 23, 2001

(54) COMPOSITIONS, METHODS, AND APPARATUS FOR DELIVERY OF A MACROMOLECULAR ASSEMBLY TO AN EXTRAVASCULAR TISSUE OF AN ANIMAL

(75) Inventor: Hansell H. Stedman, Ambler, PA (US)

(73) Assignee: The Trustees of the University of Pennsylvania, Philadelphia, PA (US)

(*) Notice: Under 35 U.S.C. 154(b), the term of this patent shall be extended for 0 days.

(21) Appl. No.: 08/954,815

(22) Filed: Oct. 21, 1997

Related U.S. Application Data

(60) Provisional application No. 60/029,292, filed on Oct. 21, 1996, and provisional application No. 60/047,919, filed on May 29, 1997.

(51) Int. Cl.$^7$ .................. A61K 38/00; A61K 31/715
(52) U.S. Cl. .................. 514/2; 514/12; 514/21; 514/44
(58) Field of Search .................. 514/44, 12, 21, 514/2; 424/85.1, 9.2, 93.2, 94.5; 536/23.1, 24.1, 23.5; 435/5, 6, 69.1, 455, 320.1

(56) References Cited

U.S. PATENT DOCUMENTS 5,384,128 * 1/1995 Meezan et al. .................. 424/450
6,007,817 * 12/1999 Epstein, et al. .................. 424/178.1

OTHER PUBLICATIONS

Rosenecker et al. Increased Liposome Extravasation . . . Proc.Natl.Acad.Sci. 93:p7236–7241, Jul. 1996.*
Parker et al. Coronary reperfusion: Effects of vasodilators (papaverine and adenosine). 93(1): 66–72, Jan. 1977.*
Acsadi et al., 1994, Hum. Molec. Genet. 3: 579–584.
Acsadi et al., 1991, Nature 352:815–819.
Boland et al., 1996, Pediatric Neurology, 14: 7–12.
Bönnemann et al., 1995, Nature Genetics 11:266–273.
Eyre, 1970, J. Pharm. Pharmacol. 22:104–109.
Graham et al., 1991, In: Methods i Molecular Biology, Murray, ed., Humana, Clifton, NJ, 109–128.
Graham et al., 1977, J. Gen. Virol. 36:59–74.
Helbling–Leclerc et al., 1995, Nature Genetics 11: 216–218.
Koening et al., 1988, Cell 53:219–228.
Kozarsky et al., 1996, Nature Genet. 13: 54–62.
Kozarsky et al., 1994, J. Biol. Chem. 268: 13695–13702.
Kozarsky et al., 1993, Som. Cell Molec. Genet. 5:449–458.
Lim et al., 1995, Nature Genetics 11: 257–265.
Majno et al., 1961, J. Biophys. Biochem. Cytol. 11:571–605
Nigro et al., 1996, Nature Genetics 14: 195–198.
Pappenheimer et al., 1951, Am. J. Physiol. 167:13–46.
Piccolo et al., 1995, Nature Genetics, 10: 243–245.
Quantin et al., 1992, Proc. Natl. Acad. Sci. 89:2581–2584.
Ragot et al., 1993, Nature 361:647–650.
Raper et al., 1996, Pancreas 12: 401–410.
Rippe et al., 1994, Physiol. Rev. 74:163–219.
Roberts et al., 1997, Cancer Res. 57:765–772.
Roberts et al., 1995, J. Cell Sci. 108:2369–2379.
Sanes et al., 1986, EMBO J. 5:3133–3142.
Senger et al., 1990, Cancer Res. 50:1774–1778.
Schlenker et al., 1991, J. Appl. Physiol. 71: 1655–1662.
Silverman et al., 1998, J. Appl. Physiol. 64:210–217.
Smith et al., 1987, New Engl. J. MEd. 316: 1197–1205.
Starling, 1896, J. Physiol. 19:312–326.
Stedman et al., 1991, Nature 352: 536–539.
Stewart et al. 1993, EMBO J. 12:2589–2599.
Thom et al., 1995, J. Clin. Oncol. 13:264–273.
Weinbaum et al., 1995, Symp. Soc. Exp. Biol. 49:323–345.
Wennmalm, 1994, J. Int. Med. 235:317–327.
Wilson, 1996, New Eng. J. Med. 334:1185–1187.
Yang et al., 1994, Nature Genetics 7: 362–369.
Yeh et al. 1996, J. Virology 70: 559–565.

* cited by examiner

*Primary Examiner*—Terry McKelvey
(74) *Attorney, Agent, or Firm*—Akin, Gump, Strauss, Hauer & Feld, L.L.P.

(57) ABSTRACT

Compositions, methods, and an apparatus are provided for delivering a macromolecular assembly such as a plasmid, virus vector, or other gene vector, to an extravascular tissue such as muscle tissue. The composition comprises the macromolecular assembly and a vascular permeability-enhancing agent. In another embodiment, the composition further comprises a vasodilating agent. The method of the invention comprises providing a vascular permeability-enhancing agent to a blood vessel and providing a macromolecular assembly to the vessel. An oxygenator useful for providing oxygen to a fluid extracorporeally prior to providing the fluid to a blood vessel of an animal is included in the invention.

44 Claims, 12 Drawing Sheets

FIG. 2A  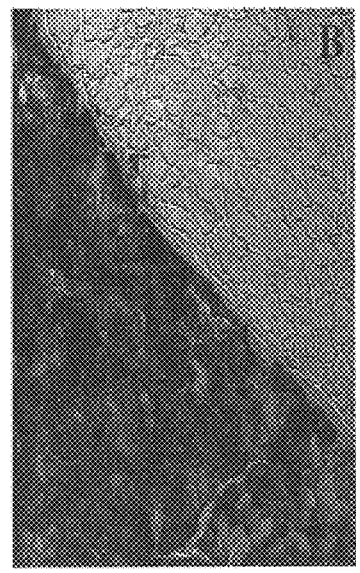 FIG. 2B
FIG. 2C 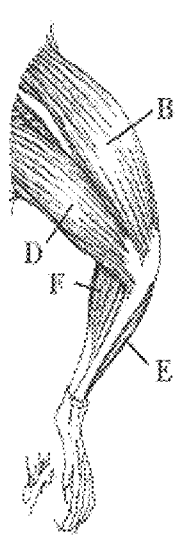 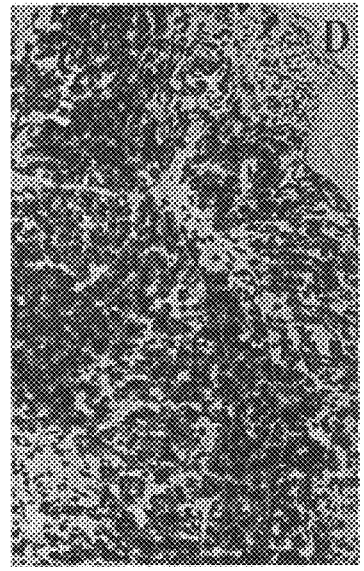 FIG. 2D
FIG. 2E 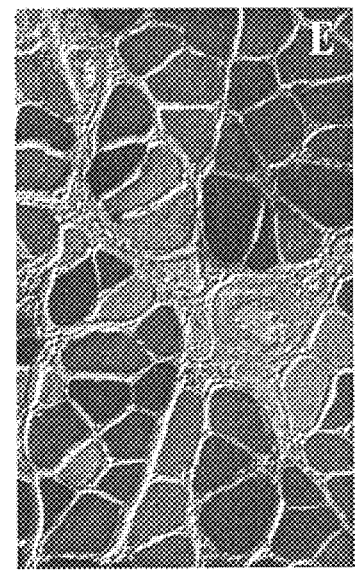  FIG. 2F

COMPOSITIONS, METHODS, AND APPARATUS FOR DELIVERY OF A MACROMOLECULAR ASSEMBLY TO AN EXTRAVASCULAR TISSUE OF AN ANIMAL

CROSS REFERENCE TO RELATED APPLICATIONS

This application claims priority under 35 U.S.C. § 119(e) to U.S. Provisional Applications Ser. Nos. 60/029,292, filed on Oct. 21, 1996, and 60/047,919, filed May 29, 1997.

GOVERNMENT SUPPORT

The invention was supported, in part by the U.S. Government (NIH Grant Nos. P30-DK 47757-03 sub 07 and P01-AR43648-01 sub 04 Project 2); the U.S. Government may therefore have certain rights in the invention.

FIELD OF THE INVENTION

The field of the invention is gene therapy.

BACKGROUND OF THE INVENTION

It is well known that viruses naturally deliver nucleic acids to cells and have therefore been exploited as gene delivery vehicles. However, in order for a recombinant virus to delivery a nucleic acid to a cell, the virus must first have access to the cell. Circulating virus in a mammal may not have ready access to cells to which it is desired that a nucleic acid be delivered. The present invention provides a means of providing to a virus access to cells to which it is desired that a nucleic acid be delivered.

The recent cloning of full length cDNAs for gene products implicated in several muscular dystrophies (Lim et al., 1995, Nature Genetics 11: 257–265; Piccolo et al., 1995, Nature Genetics, 10: 243–245; Nigro et al., 1996, Nature Genetics 14: 195–198; Bonnemann et al., 1995, Nature Genetics 11: 266–273; and Helbling-Leclerc et al., 1995, Nature Genetics 11: 216–218) has been paralleled by improvement in a variety of virus-based vector systems for use in somatic gene transfer (Yang et al., 1994, Nature Genetics 7: 362–369; Yeh et al. 1996, J. Virology 70: 559–565; and Wilson, 1996, New Eng. J. Med. 334:1185–1187). The universal muscle involvement and resulting respiratory insufficiency in these diseases have focussed attention on the need for systemic vector delivery in vivo to animal tissues and organs (Boland et al., 1996, Pediatric Neurology, 14: 7–12; Stedman et al., 1991, Nature 352: 536–539.; Schlenker et al., 1991, J. Appl. Physiol. 71: 1655–1662; and Smith et al., 1987, New Engl. J. Med. 316: 1197–1205). Under physiologic conditions, the continuous endothelium of the skeletal muscle microvasculature is virtually impermeable to proteins larger than albumin (Stokes radius 3.5 nanometers; Berne et al., 1992, In: Physiology, Mosby, St. Louis), and the underlying basal lamina restricts the diffusion of larger macromolecular aggregates (Majno et al., 1961, J. Biophys. Biochem. Cytol. 11:571–597).

There is an acute need to develop compositions and methods which facilitate access of large macromolecules to muscle for the purposes of delivery of compounds which are of therapeutic benefit to mammals in need of such compounds. The present invention satisfies this need.

SUMMARY OF THE INVENTION

The invention relates to a composition for delivering a macromolecular assembly to an extravascular tissue of an animal comprising the macromolecular assembly and a vascular permeability-enhancing agent. In one embodiment, the macromolecular assembly is a gene vector. In another embodiment, the vascular permeability-enhancing agent is selected from the group consisting of histamine, acetylcholine, an adenosine nucleotide, arachidonic acid, bradykinin, cyanide, endothelin, endotoxin, interleukin-2, ionophore A23 187, nitroprusside, a leukotriene, an oxygen radical, phospholipase, platelet activating factor, protamine, serotonin, tumor necrosis factor, vascular endothelial growth factor, a venom, and a vasoactive amine, and is preferably histamine or vascular endothelial growth factor.

In another aspect of the invention, the composition comprises the macromolecular assembly a vascular permeability-enhancing agent, and a vasodilating agent. In one embodiment, the vasodilating agent is selected from the group consisting of papaverine, nimodipine, hydralazine, nitric oxide, epoprostenol, tolazoline, amrinone, milrinone, nitroglycerine, isosorbide dinitrate, isosorbide mononitrate, and an organic nitrate compound, and is preferably papaverine.

In yet another aspect of the invention, the composition comprises the macromolecular assembly a vascular permeability-enhancing agent, and an oxygen-transporting agent.

The invention also provides a kit for providing a macromolecular assembly to an extravascular tissue of an animal. The kit comprises a vascular permeability-enhancing agent and a vasodilating agent. In one embodiment, the kit further comprises the macromolecular assembly. In another embodiment, the macromolecular assembly is a gene vector comprising a human gene selected from the group consisting of a gene encoding dystrophin, a gene encoding eutrophin, a gene encoding a sarcoglycan, and a gene encoding a minidystrophin.

In yet another aspect, the kit comprises a vascular permeability-enhancing agent, a vasodilating agent, and an oxygen-transporting agent.

In a further aspect of the invention, the kit comprises a vascular permeability-enhancing agent, a vasodilating agent, and at least one disposable element of an extracorporeal circulatory support and oxygenation system. In one embodiment, the at least one disposable element is an oxygenator having a hollow body, a liquid inlet in fluid communication with the interior of the body, a liquid outlet in fluid communication with the interior of the body, a gas inlet for providing gas to the interior of a gas chamber, at least one gas-permeable membrane separating the gas chamber from the interior of the body, and a gas outlet for permitting gas to exit from the gas chamber, whereby gas exchange is enabled between a fluid in the interior of the body and a gas in the gas chamber. In another embodiment of the kit comprising an oxygenator, the body is a tube, the gas-permeable membrane comprises polytetrafluoroethylene (PTFE) tubing extending within at least a portion of the tube, and the gas chamber comprises the interior of the PTFE tubing.

The invention further relates to a method of delivering a macromolecular assembly to an extravascular tissue of an animal, preferably a human. The method comprises the steps of providing a vascular permeability-enhancing agent to a blood vessel associated with the tissue to increase the permeability of the endothelial layer of the vessel and providing the macromolecular assembly to the vessel, whereby the assembly is delivered to the tissue through the endothelial layer of the vessel. In one embodiment of the method, the macromolecular assembly is a gene vector, preferably an adenoviral gene vector. The gene vector preferably comprises a human gene, such as a gene selected from the group consisting of a gene encoding human dystrophin, a gene encoding eutrophin, a gene encoding a sarcoglycan, and a gene encoding a minidystrophin. In another embodiment, the gene vector comprises a promoter/regulatory region operably linked to the human gene, wherein the promoter/enhancer region is selected from the group consisting of a human skeletal muscle creatine phosphokinase promoter/regulatory region, a murine skeletal muscle creatine phosphokinase promoter/regulatory region, a promoter/regulatory region of a gene which is ordinarily expressed in a human skeletal muscle cell, and a human constitutive promoter region.

In another aspect of the invention, the method further comprises the step of providing a vasodilating agent to the vessel.

In another aspect of the invention, the tissue to which the macromolecular assembly is delivered is muscle tissue, preferably striated muscle tissue.

In yet another aspect, the method further comprises the step of increasing the perfusion pressure within the vessel above the normal physiological perfusion pressure after providing the macromolecular assembly to the vessel.

In still another aspect, the method further comprises the step of isolating the vessel from the blood circulatory system of the animal prior to providing the macromolecular assembly to the vessel. In one embodiment, the step of isolating the vessel from the blood circulatory system of the animal is performed prior to providing the vascular permeability-enhancing agent to the vessel. In another embodiment, the method further comprises the step of providing a clearance solution to the vessel after providing the macromolecular assembly to the vessel, the clearance solution being substantially free of the vascular permeability-enhancing agent.

In another aspect, the method further comprises the step of providing an oxygen-transporting agent to the vessel after isolating the vessel from the blood circulatory system.

In yet another aspect, the method further comprises the step of subjecting the animal to extracorporeal circulatory support and oxygenation prior to providing the vascular permeability-enhancing agent.

In still another aspect, the method further comprises the step of occluding the blood supply to the liver of the animal prior to providing the macromolecular assembly.

The invention also relates to a method of delivering a gene vector to an extravascular tissue of an animal, the method comprising the steps of
a) isolating a blood vessel associated with the tissue from the blood circulatory system of the animal;
b) thereafter providing a vasodilating agent to the vessel;
c) thereafter providing a vascular permeability-enhancing agent to the vessel to increase the permeability of the endothelial layer of the vessel;
   providing the gene vector to the vessel, whereby the vector is delivered to the tissue through the endothelial layer of the vessel;
   increasing the perfusion pressure within the vessel above the normal physiological perfusion pressure; and
   providing an oxygen-transporting agent to the vessel; and
d) thereafter providing a clearance solution to the vessel, the clearance solution being substantially free of the vascular permeability-enhancing agent.

The invention further relates to a method of providing a gene vector to substantially all muscle tissues of an animal, the method comprising the steps of a) subjecting the animal to extracorporeal circulatory support and oxygenation;
b) thereafter providing a vasodilating agent to the blood circulatory system of the animal;
   providing a vascular permeability-enhancing agent to the blood circulatory system to increase the permeability of the endothelial layer of the vessels of the blood circulatory system;
   providing the gene vector to the blood circulatory system, whereby the vector is delivered to substantially all muscle tissues through the endothelial layer of the vessels of the blood circulatory system; and
   increasing the perfusion pressure within the vessel above the normal physiological perfusion pressure.

BRIEF DESCRIPTION OF THE DRAWINGS

FIG. 1a is an image depicting, at 500× magnification, marker gene activity in the biceps femoris of an adult rat four days after arterial infusion of AdCMVlacZ (Table 1, series C) as assessed by staining with Xgal.

FIG. 1b is an image depicting, at 350× magnification, marker gene activity in the tibialis anterior of an adult rat as assessed by Xgal staining at higher pressure infusion (Table 1 series e).

FIG. 1c is an image depicting, at 500× magnification, marker gene activity in the tibialis anterior of an adult rat as assessed by Xgal staining of a whole mount specimen. Focal gene transduction limited to this portion of the tibialis anterior was the result of intramuscular injection of $5 \times 10^{10}$ particles of AdCMVlacZ three days prior to obtaining the image.

FIGS. 2A–2F are a series of images depicting highly efficient gene transfer to adult rat skeletal muscle fibers following gene vector delivery in the presence of histamine and papaverine. Panel A is an image depicting the entire hindlimb from a rat which was dissected before whole mount staining to expose multiple cross sections. Panel B is an image depicting marker gene distribution in the quadriceps (top row in Panel A) as assessed by light microscopy at 100× magnification. This image illustrates that placement of a tourniquet at the level of the common femoral artery occludes primary blood supply to the rectus femoris. Panel C is an image which illustrates the relative positions of muscle groups depicted in the images shown collectively in FIG. 2. Panel D is an image which depicts, at 25× magnification, the semimembranosus, the adductor brevis, and the adjacent saphenous artery (in the upper right of the Panel). Panel E is an image depicting a 300× Nomarski micrograph of a portion of the tibialis anterior, and depicts the unstained wall of arteriole (in the left center portion of the Panel) and numerous uniformly stained muscle fibers. Panel F is an image depicting, at 25× magnification, the gastrocnemius following gene delivery thereto.

FIG. 6b is a graph which summarizes physiological data obtained from an approximately 40 kilogram sheep to which 300 milligrams of papaverine and 5 grams of histamine were administered. Abbreviations are the same as in FIG. 6a.

DETAILED DESCRIPTION OF THE INVENTION

Figure 1A:
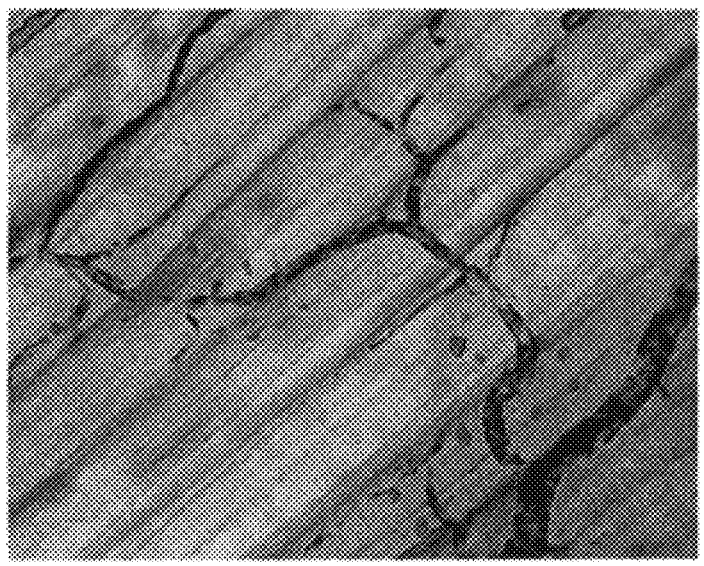
FIGS. 1A–1C are images depicting patterns of gene transfer in rat muscle in the absence of inflammatory mediators and demonstrates the integrity of the vascular endothelial barrier to adenovirus transport.

The invention includes compositions, methods, and an apparatus for delivering a macromolecular assembly such as a gene vector, to an extravascular tissue, such as muscle tissue. The compositions, methods, and apparatus of the invention involve the use of a vascular permeability-enhancing agent to alter the permeability of the endothelial layer of blood vessels of the vascular system. In some aspects of the invention, the compositions, methods, and apparatus involve the use of a vasodilating agent to improve the ability of the macromolecular assembly to be delivered to portions of a blood vessel that would, in the absence of the vasodilating agent, be too narrow to accommodate the assembly. Thus, in some aspects, the compositions, methods, and apparatus of the invention involve the use of both a vasodilating agent to improve delivery of a gene transfer vector to ordinarily inaccessible portions of a blood vessel and a vascular permeability-enhancing agent to improve passage of the vector through the endothelial layer of the vessel. Compositions useful for performing the method of the invention are provided, as is an apparatus comprising an oxygenator and a kit comprising one or more compositions and/or apparatus(es) for performing the method of the invention.

The invention is exemplified by the use of an adenovirus as a gene delivery vector, the use of a vascular permeability-enhancing agent such as histamine, and the use of a vasodilating agent such as papaverine, to alter microvascular access and permeability. Thus, while the invention is not limited to the use of adenovirus vectors as gene delivery vehicles, the invention is exemplified by the use of adenovirus vectors to demonstrate the efficacy of the compositions, methods, and apparatus which have been developed to enhance microvascular access and permeability with respect to macromolecular assemblies. The invention should therefore not be construed to be limited solely to the use of adenoviruses as a gene delivery vehicle or to the use of histamine and papaverine as a means of altering microvascular access and permeability.

The continuous endothelium of the blood vessels which provide blood supply to skeletal muscle tissue blocks egress of an adenovirus from the vascular space to the muscle tissue. Different staining patterns arise after a marker virus is injected into the femoral artery upstream of a series of muscle fibers, as compared with the staining patters which arise after the marker is injected directly into the interstitium of the muscle fibers.

It has been hypothesized by others that adenovirus vector uptake by cells of an extravascular tissue is dependent wholly or primarily upon the presence on those cells of a virus receptor protein which is specifically bound by the vector, thereby facilitating uptake. Thus, it has been previously thought that adenovirus vectors were poor vectors for gene delivery to muscle tissue via the blood circulatory system of an animal on account of a dearth of appropriate adenovirus receptor proteins on muscle cells. The data presented herein, as well as the observation that adenovirus vectors delivered directly to muscle tissue, for example, by direct injection of a vector suspension into muscle tissue, demonstrate that the ability of an adenovirus vector to deliver a gene to muscle tissue via the bloodstream is far more dependent upon the ability of the vector to penetrate the endothelial layer of the blood vessel than upon the presence of an adenovirus receptor protein on the surfaces of the cells of the tissue.

The appearance of mouse liver at necropsy following adenovirus gene vector delivery via the bloodstream, the effects of the Pringle maneuver upon the appearance of the mouse liver, and the discontinuity of the hepatic microvasculature, establish that the endothelial wall of the blood capillaries supplying the liver have discontinuities of up to one micron in diameter. These discontinuities accommodate chylomicrons of up to 600 nanometers in diameter, as indicated by the fact that they pass freely from the vascular space into the spaces around hepatocytes. The liver therefore removes, by a process analogous to filtration, particles of any sort including, for example, a circulating adenovirus gene vector. Where delivery of an adenovirus gene vector to an extravascular tissue such as striated muscle is desired, sequestration of the vector in the liver is undesirable. Thus, it has been discovered in the present invention that performance of the Pringle maneuver in conjunction with supplying a macromolecular assembly such as, for example, an adenovirus gene vector, to the bloodstream of an animal, reduces hepatic sequestration of the assembly, enabling more efficient delivery of the assembly to a desired extravascular tissue such as muscle tissue.

Skeletal muscle is a highly vascular tissue. Since muscle performs a unique physiological role for the animal, the extreme vascularity would appear to be an advantage to the gene therapist. The tissue has the greatest metabolic scope of all tissues, the metabolic scope being the ratio of the basal metabolic rate in nonstimulated tissue compared with its metabolic rate following maximal stimulation. For example, the resting metabolic rate in skeletal muscle tissue is equivalent to hydrolysis of about 2 micromoles of adenosine triphosphate per gram of wet tissue per minute. At maximal stimulation, the metabolic rate is equivalent to hydrolysis of about 120 micromoles of adenosine triphosphate per gram of wet tissue per minute. During anaerobic sprint, the metabolic rate is equivalent to hydrolysis of about 480 micromoles of adenosine triphosphate per gram of wet tissue per minute. Importantly, most capillaries in skeletal muscle tissue are not perfused at rest. Nonetheless, skeletal muscle is the preferred tissue for free tissue transfer in reconstructive surgery because of its vascularity.

Striated muscle is a formidable target for gene transfer. It comprises about half of the body weight of most mammals. Cardiac muscle is a form of striated muscle. Patients afflicted with muscular dystrophy are also afflicted with heart disease. Muscle is supplied with blood by blood vessels having a continuous epithelium. Under ordinary physiological conditions, the epithelial layer of these blood vessels is virtually impermeable to albumin, a protein having a Stokes radius of about 3 nanometers, which is about one thirtieth the radius of an adenovirus, which has a Stokes radius of about 70–90 nanometers. Thus, it is necessary that the permeability of the endothelial layer of the blood vessels which supply blood to muscle tissue be significantly increased relative to the layer's permeability under ordinary physiological conditions, if adenovirus gene vectors are to be permitted to pass through the layer.

Muscle is a very vascular tissue comprising much greater than half of the total capillary surface area in a mammalian body. Consequently, if the endothelium of muscle suddenly becomes permeable to albumin-sized molecules, circulatory collapse ensues in the absence of extracorporeal circulatory support, and the mammal experiences shock. Thus, the endothelial barrier is critical to homeostasis of the circulating blood volume. During normal circulatory homeostasis, the flow rate of blood past individual cells in the body provides oxygen at a rate which is adequate to meet the individual demands of the cell. During shock, this flow rate falls below that level to a non-sustainable level resulting in oxygen starvation of cells and, if the shock persists for a sufficient length of time, cell death ensues.

Endothelial pathophysiology, i.e., dysfunction of the walls of the microcirculatory channels in the body, occurs in a wide range of pathological states including inflammation, systemic anaphylaxis, septic shock, cardiopulmonary bypass, carcinoid syndrome, and carcinoid crisis. Each of these states involves an increase in vascular endothelial permeability which allows not only water, cations, and anions, but also large macromolecules to permeate the endothelial barrier.

The present invention is premised upon the observation that vascular endothelial permeabilization facilitates transfer of a macromolecular assembly, such as an adenovirus gene vector, from the vascular space across the vascular endothelium to an extravascular tissue, such as muscle tissue. As is described herein, vascular endothelial permeability can be pharmacologically enhanced. Therefore, it is possible to manipulate endothelial permeability using a vascular permeability-enhancing agent such as an inflammatory mediator or a derivative thereof, without necessarily inducing anaphylactic shock. Vascular permeability-enhancing agents are the mediators of choice because of the rapidity with which they act to alter endothelial permeability and the reversibility of their action.

The composition of the invention comprises a macromolecular assembly, such as a gene delivery vector, and a vascular permeability-enhancing agent. Preferred gene delivery vectors are virus vectors, more particularly adenovirus vectors.

Preferably, such a gene vector comprises a human gene, such as the gene encoding dystrophin, a gene encoding eutrophin, a gene encoding a sarcoglycan, or a gene encoding a minidystrophin. The gene vector may also comprise a promoter/regulatory region operably linked to the human gene, such as the human skeletal muscle creatine phosphokinase promoter/regulatory region, the murine skeletal muscle creatine phosphokinase promoter/regulatory region, a promoter/regulatory region of a gene which is ordinarily expressed in a human skeletal muscle cell, or a human constitutive promoter region. Methods of constructing gene vectors are well known in the art.

Preferable vascular permeability-enhancing agents are those which alter permeability of the vascular endothelium to the extent that the endothelium will accommodate a virus vector having a diameter of approximately 100 nanometers. Numerous vascular permeability-enhancing agents are known, including, but not limited to, histamine, acetylcholine, adenosine nucleotides, arachidonic acid, bradykinin, cyanide, endothelin, various endotoxins, interleukin-2, ionophore A23187, nitroprusside, various leukotrienes, oxygen radicals, phospholipases, platelet activating factor, protamine, serotonin, tumor necrosis factor, vascular endothelial growth factor (VEGF), numerous venoms, and numerous vasoactive amines. Of the agents listed herein, two are preferred, namely histamine and VEGF.

Histamine has been widely characterized, and its pharmacologic properties are relatively well understood. As described herein, histamine is an efficacious agent for enhancing vascular endothelial permeability to the extent that an adenovirus gene vector can pass from the bloodstream to an extracellular tissue. Hence, histamine is a preferred vascular permeability-enhancing agent of the invention. Administration of histamine to a mammal has numerous known and undesirable side effects. Numerous compositions, such as antihistamines and histamine receptor antagonists, are known which are useful for reversing or alleviating the side effects of histamine in a mammal. The use of such compositions, either in conjunction with or following administration of histamine to an animal is contemplated as a variant of the invention. While not wishing to be bound by any particular theory, it is believed that certain antihistaminic agents act by blocking, reversing, or antagonizing the binding of histamine to one or more species of histamine receptor, such as an H1 or an H2 receptor of histamine while not affecting the interaction of histamine with one or more other histamine receptors. Thus, certain antihistaminic agents may be particularly useful for preventing or reversing the undesirable side effects of administering histamine to an animal while not affecting the vascular permeability-enhancing properties of histamine. Administration of such antihistaminic agents in conjunction with or following administration of histamine in the compositions, methods, and apparatus of the invention is contemplated in the present invention.

VEGF has been demonstrated to be a vascular permeability-enhancing agent that is efficacious at a far lower concentration than is histamine. Furthermore, VEGF does not induce all of the undesirable side effects induced by histamine (Roberts et al., 1995, J. Cell Sci. 108:2369–2379; Roberts et al., 1997, Cancer Res. 57:765–772; Sanger et al., 1990, Cancer Res. 50:1774–1778). Hence, VEGF is a preferred vascular permeability-enhancing agent of the invention.

The invention is also premised upon the observation that vasodilation of capillary beds improves the efficiency of gene transfer from the vascular space across the vascular endothelium to an extravascular tissue. This effect is less critical in liver due to the fenestration of this organ, but is crucial in the case of other extravascular tissues, such as muscle tissue, wherein most of the capillaries are not perfused at rest. Vasodilation causes broadening of the lumen of capillaries and, without being bound by any particular theory of operation, may also cause or improve fenestration of the vascular endothelium. Thus, vasodilation improves exudation from a blood vessel into an extravascular tissue. As described herein, a vasodilating compound improves delivery of a vascular permeability-enhancing agent to narrow portions of a blood vessel, thereby improving the efficacy of the agent by permitting it to act upon a greater proportion of the vessel's endothelial surface. Vasodilation also improves delivery of a macromolecular assembly to narrow portions of a blood vessel, thereby permitting improved transepithelial delivery of the assembly due to increased epithelial surface area available for such delivery. Numerous vasodilating agents are known in the art, including, but not limited to, papaverine, nimodipine, hydralazine, epoprostenol, nitric oxide, tolazoline, amrinone, milrinone, nitroglycerine, isosorbide dinitrate, isosorbide mononitrate, and numerous organic nitrate compounds.

Thus the present invention contemplates a composition comprising a macromolecular assembly, such as a gene delivery vector, a vascular permeability-enhancing agent, and a vasodilating agent. Preferably, the vasodilating agent is papavenne.

In one embodiment, the composition of the invention comprises a pharmaceutically-acceptable carrier, such as an isotonic buffering agent or the like. The composition may be administered to an animal to deliver an amount of the macromolecular assembly in the range from one nanogram per kilogram of body weight per day to one hundred milligrams per kilogram of body weight per day. The composition may be administered in a single dose or in multiple doses, the multiple doses administered over a course of days, weeks, or months.

The vascular permeability-enhancing agent or the vasodilating agent or both of the composition of the invention may be provided to a blood vessel of an animal in the form of a pharmaceutical composition. Pharmaceutical compositions that are useful in the methods of the invention may be administered systemically in oral solid formulations, ophthalmic, suppository, aerosol, topical or other similar formulations. In addition to the vascular permeability-enhancing agent or the vasodilating agent or both, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the vascular permeability-enhancing agent or the vasodilating agent or both according to the methods of the invention.

In another embodiment, the composition of the invention further comprises an oxygen-transporting agent, so that oxygen may be delivered to the extravascular tissue, for example, during exposure of the tissue to the gene delivery vector. Any oxygen-transporting agent known in the art may be used, including, but not limited to, the blood of the animal to which the composition is being administered, blood from a different individual of the same type of animal, a perfluorochemical liquid, a hemoglobin-containing composition, or the like.

The composition of the invention may be provided in the form of a kit for delivering a macromolecular assembly to an extravascular tissue of an animal, the kit comprising a vascular permeability-enhancing agent and a vasodilating agent. Preferably, the vascular permeability-enhancing agent is histamine or vascular endothelial growth factor and the vasodilating agent is papaverine. Where the kit is intended to be used to deliver a gene vector to an extravascular tissue, the kit may also comprise the gene vector, such as an adenovirus vector. Preferably, such a gene vector comprises a human gene, such as the gene encoding dystrophin, a gene encoding eutrophin, a gene encoding a sarcoglycan, or a gene encoding a minidystrophin. The gene vector may also comprise a promoter/regulatory region operably linked to the human gene, such as the human skeletal muscle creatine phosphokinase promoter/regulatory region, the murine skeletal muscle creatine phosphokinase promoter/regulatory region, a promoter/regulatory region of a gene which is ordinarily expressed in a human skeletal muscle cell, or a human constitutive promoter region. Methods of constructing gene vectors are well known in the art.

The invention is further premised on the observation that mechanical circulatory support and extracorporeal oxygenation extends the pharmacological range of the composition of the invention. In other words, if a mammal is connected to a heart-lung machine, it is possible to do all of the following. The heart is protected functionally from the effects of the vascular permeability-enhancing agent and the effects of any vasodilating agent included in the composition. Massive vasodilatation in the absence of extracorporeal support results in reflex tachycardia and increased contractility to the heart, both of which would cause damage to an already genetically deficient heart, such as the heart of a human afflicted with muscular dystrophy. Furthermore, extracorporeal circulation permits independent control of pulmonary perfusion pressure, including that within the pulmonary artery. Placement of a large canula in the right atrium of a human heart permits withdrawal of blood from the right atrium prior to right ventricular filling during cardiac diastole. This reduces systolic pulmonary artery pressure and decreases exudation from blood vessels into the pulmonary parenchyma, thereby preventing fluid accumulation in the lungs of the human. This is important to minimize the acute morbidity of the intervention. The extracorporeal circuit also ensures vascular access for rapid replacement of fluid which passes from the bloodstream to an extravascular tissue during exudation, and permits maintenance of adequate tissue oxygenation throughout the body during the procedure. The oxygenation provided by the heart-lung machine is independent of the alveolar-to-arterial gradient, thereby circumventing hypoxyemia associated with pulmonary edema. In other words, blood which is circulating through the extracorporeal pump can be fully oxygenated prior to delivery to the body. The extracorporeal circuit can also be instituted by a minimally invasive access route.

Figure 8:
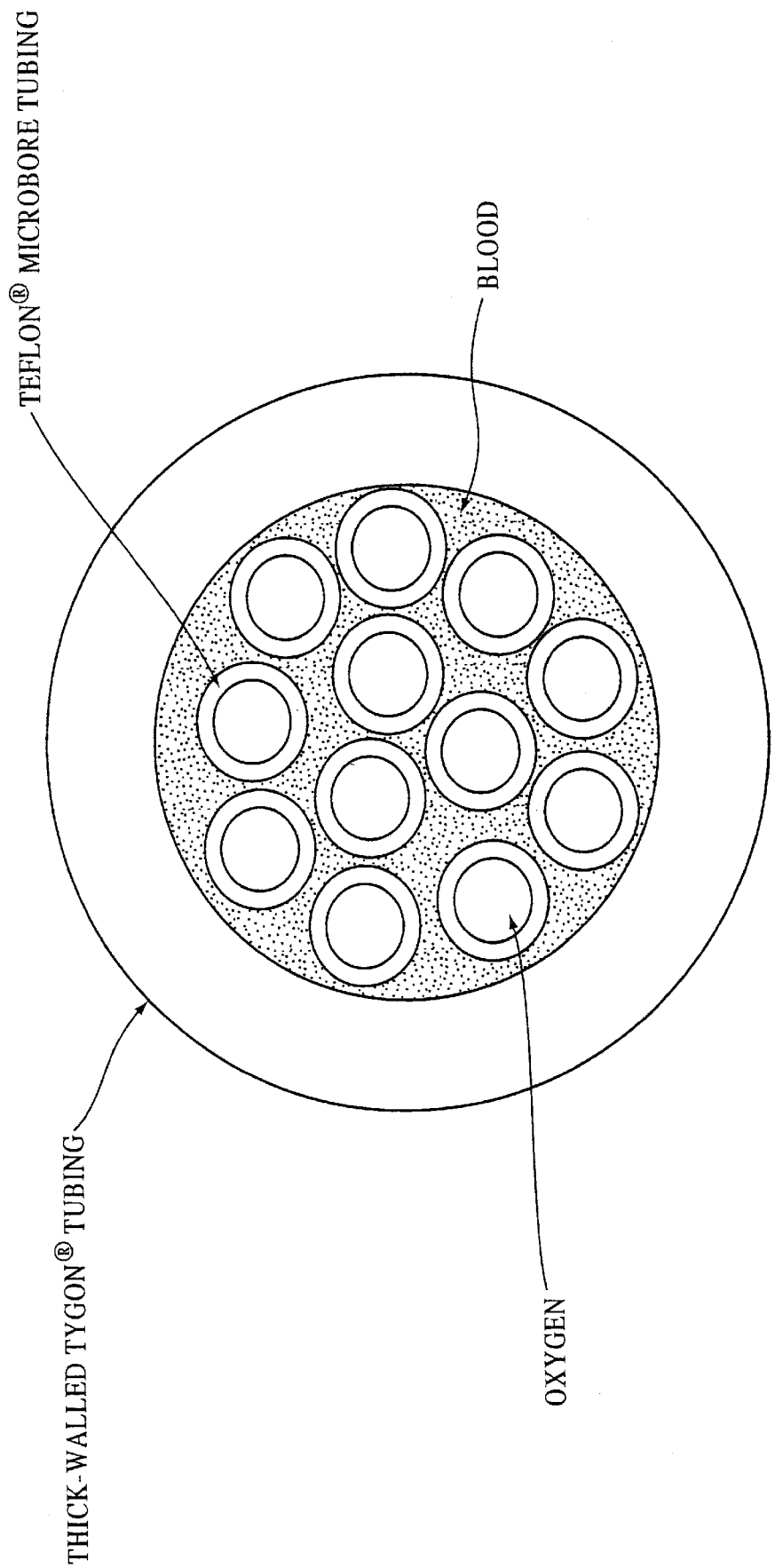
FIG. 8 is a diagram which illustrates the operation of one embodiment of the oxygenator depicted in FIG. 7.
Figure 9A:
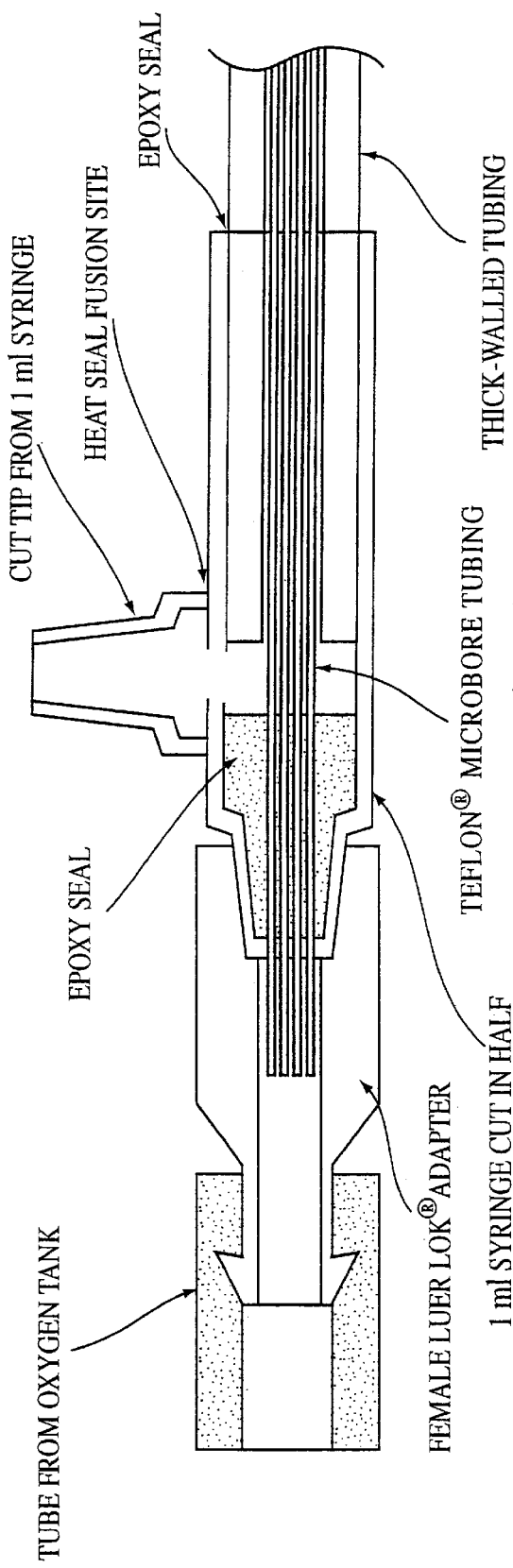
FIG. 9 is a diagram which illustrates the construction of one embodiment of the oxygenator depicted in FIG. 7.
Figure 9B:
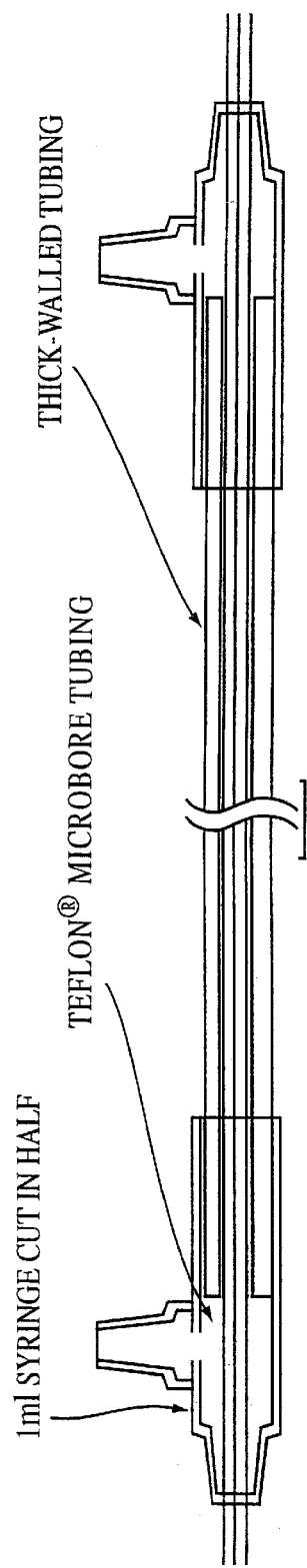
Figure 10:
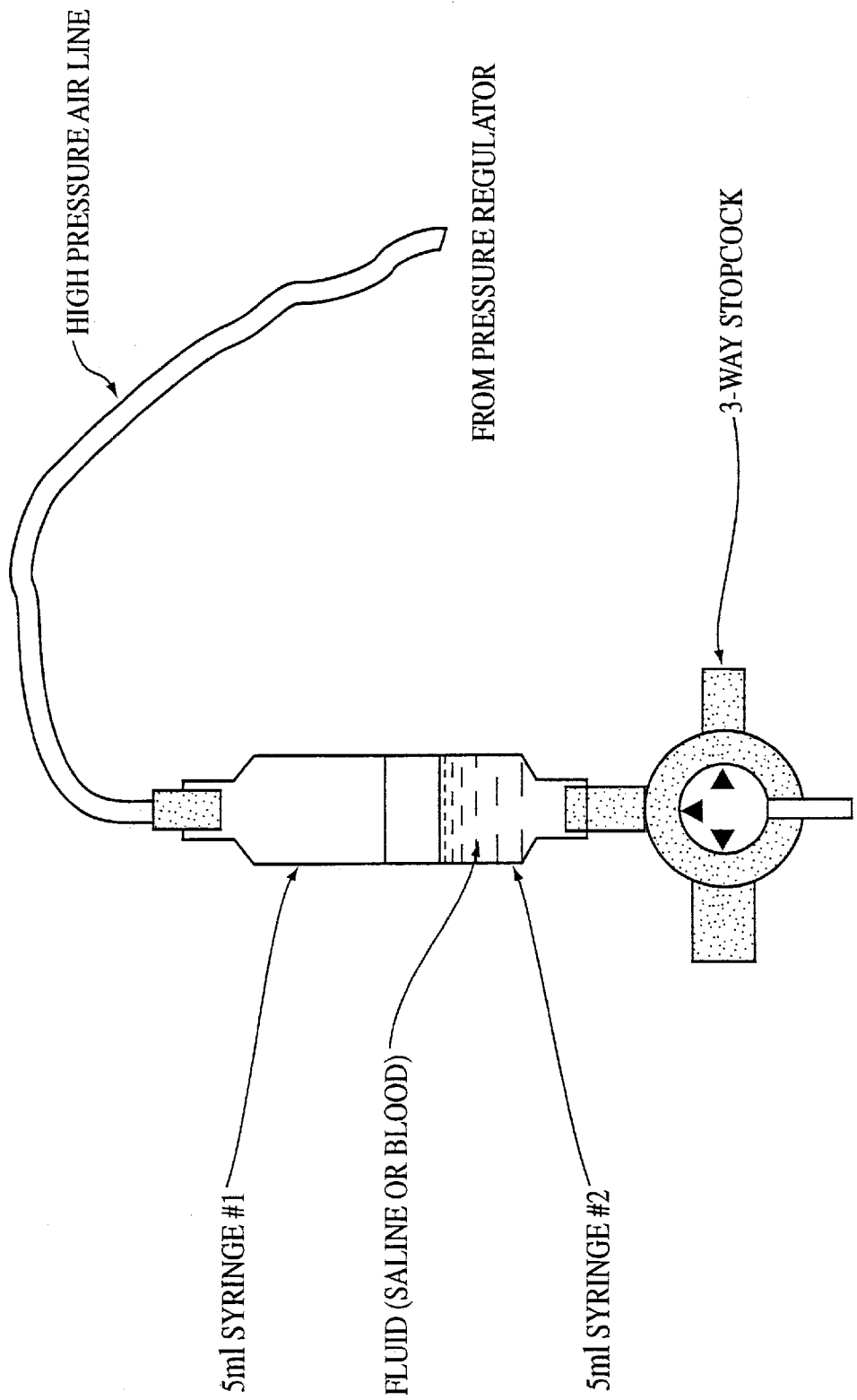
FIG. 10 is a diagram which illustrates the construction of one embodiment of the interface between the pressure regulator and the delivery mechanism depicted in FIG. 7.

Thus, the kit of the invention may also comprise an oxygen-transporting agent or at least one disposable element of an extracorporeal circulatory support and oxygenation system. For example, the at least one disposable element may be an oxygenator having a hollow body, a liquid inlet in fluid communication with the interior of the body, a liquid outlet in fluid communication with the interior of the body, a gas inlet for providing gas to the interior of a gas chamber, at least one gas-permeable membrane separating the gas chamber from the interior of the body, and a gas outlet for permitting gas to exit from the gas chamber, whereby gas exchange is enabled between a fluid in the interior of the body and a gas in the gas chamber. The oxygenator may be constructed analogously to that illustrated in FIGS. 8 and 9, wherein the gas-permeable membrane comprises PTFE tubing extending within at least a portion of the tube, and wherein the gas chamber comprises the interior of the PTFE tubing.

A kit which is useful for performing the method of the invention is contemplated which comprises, in addition to the composition of the invention, at least one disposable element of an extracorporeal circulatory support and oxygenation system and at least one cannula for providing the composition of the invention to a blood vessel of an animal. Preferably, such a kit comprises all of the single-use components needed to perform the method of the invention, including a macromolecular assembly, a vascular permeability-enhancing agent, a fluid delivery instrument such as a syringe or a length of peristaltic pump tubing, and a cannula such as a hollow bore needle adapted to fit a syringe. Such a kit may also comprise a vasodilating agent, a pharmaceutically acceptable carrier, a second cannula, an oxygen-transporting agent, a clearance solution which is substantially free of the vascular permeability-enhancing agent, one or more blood vessel occluding devices, such as a clamp, hemostat, or tourniquet, a disposable oxygenator, and the like.

The method of the invention is a method of delivering a macromolecular assembly such as a gene vector to an extravascular tissue of an animal. The method comprises the steps of providing a vascular permeability-emhancing agent to a blood vessel associated with the tissue to increase the permeability of the endothelial layer of the vessel and providing the gene vector to the vessel, whereby the vector is delivered to the tissue through the endothelial layer of the vessel. The vascular permeability-enhancing agent may be provided to the vessel simultaneously with the vector, or may be provided to the vessel before or after the vector is provided. Preferably, the vascular permeability-enhancing agent is histamine or VEGF. By way of example, a composition comprising 10 millimolar histamine and an adenovirus vector may be provided to a blood vessel of an animal, wherein the histamine enhances the permeability of the blood vessel, whereby the adenovirus vector can pass through the endothelial layer of the blood vessel to an extravascular tissue, such as a muscle which is adjacent the blood vessel. The concentration of the vascular permeability-enhancing agent which is used in the method depends on the identity of the agent, but must be sufficient to enhance the permeability of the blood vessel, such that after exposure to the agent, the vessel has a greater permeability than it does before exposure to the agent. Useful concentrations of vascular permeability-enhancing agents are known in the art.

In another embodiment, the method of the invention further comprises providing a vasodilating agent to the vessel, preferably prior to providing the gene vector to the vessel, and also preferably prior to providing the vascular permeability-enhancing agent. The vasodilating agent may be provided before, during, or after provision of the composition of the invention. The concentration of the vasodilating agent is not critical, although it must be sufficiently great to induce vasodilation in the vessel. As noted herein, numerous vasodilating agents are known in the art, as are the concentrations of those agents which are useful for promoting vasodilation. It is contemplated that a higher concentration of the vasodilating agent may be used when the animal to which the vasodilating agent is administered is subjected to mechanical circulatory support to compensate for the physiological side effects of the vasodilating agent. The use of papaverine in the method of the invention is preferred.

The method of the invention may be used to deliver a macromolecular assembly to any extravascular tissue including, but not limited to, muscle tissue, striated muscle tissue, cardiac muscle tissue, bone tissue, bone marrow tissue, skin tissue, brain tissue, and the like. As noted herein, it is not necessary to use the method of the invention to deliver such an assembly to certain fenestrated extravascular tissues, such as liver and spleen. Nonetheless, the method of the invention may be used to deliver a macromolecular assembly to any extravascular tissue, whether fenestrated or not.

The animal to which the composition of the invention is provided is preferably a mammal, and even more preferably a human. Provision of the composition of the invention to a human afflicted with muscular dystrophy is particularly contemplated.

In a variation of the method of the invention, the perfusion pressure within the blood vessel is increased above the normal physiological perfusion pressure after providing the gene vector to the vessel. The increase in perfuision pressure may be within the range from 5 to 80 pounds per square inch or more. However, it is recognized that the greater the increase in perfusion pressure, the greater is the risk of structural damage to vascular and extravascular tissues. Nonetheless, one skilled in the art is able, using the information disclosed herein, to weigh the benefit to be gained by increasing perfusion pressure and the corresponding risk of tissue damage. It is contemplated that in situations in which a blood vessel has been isolated from the blood circulatory system of an animal, and particularly from the animal's heart, the risk of injury to the animal is less dependent upon the increase in perfusion pressure, compared with the situation in which the blood vessel is not so isolated.

Blood vessel occlusion is useful in the method of the invention for a number of reasons. As described in the preceding paragraph, isolating a blood vessel prior to increasing the pressure in that vessel can minimize the pressure increase in other blood vessels and tissues of the animal. Occlusion of the blood vessel to which the composition of the invention is provided can also minimize the amount of the composition that is available to the circulatory system of the animal or to other tissues of the animal. Particularly where a composition comprises an amount of a vascular permeability-enhancing agent or a vasodilating agent which would be harmful to the animal if provided to the circulatory system of the animal, sequestration of the composition to the desired blood vessel is beneficial, and can be achieved by occluding the desired blood vessel prior to providing the composition to the vessel. It may also be useful to provide a composition comprising an oxygen-transporting agent to the vessel if occlusion is to persist for more than a few minutes. It may be useful to continue occluding the blood vessel until the vascular permeability-enhancing agent, the vasodilating agent, or both have been metabolized to non-harmful levels.

Alternately, a clearance composition may be provided to the blood vessel following provision to the vessel of the composition of the invention. The clearance composition is substantially free of the vascular permeability-enhancing agent, and is preferably free of any vasodilating agent that was present in the composition of the invention. Provision of the clearance composition to the vessel after provision of the composition of the invention to the vessel can serve to dilute or 'wash out' any vascular permeability-enhancing agent or vasodilating agent which was provided to the vessel, but which was not metabolized or absorbed by a tissue of the animal. Preferably, a plurality of individual aliquots of the clearance composition is provided to the blood vessel in a sequential fashion.

Particularly in situations in which the composition of the invention is provided to the blood circulatory system of an animal, or to a portion of that system including the hepatic blood flow vessels, it may be useful to occlude blood vessels which supply tissues capable of sequestering the macromolecular assembly of the composition. For instance, as described herein, transient hepatic flow occlusion minimizes adenovirus vector sequestration. The Pringle maneuver involves the placement of the surgeon's forefinger behind the hepatoduodenal ligament so that the thumb can occlude against the finger the two major vessels providing blood supply to the liver, namely the hepatic artery and the portal vein. It is possible to perform this procedure in humans as young as about one year of age, and up to one hour of hepatic inflow occlusion is known to be tolerated.

Any method of occluding flow through a blood vessel may be used in the method of the invention. Numerous occlusion methods are known in the art, including digital occlusion wherein a surgeon occludes a blood vessel by applying finger pressure, use of a clamp, use of a hemostat, use of a tourniquet, use of an angiographically- or radiographically-placed balloon, and the like.

Where it is desired to provide the composition to the systemic blood circulation of an animal, but not to the lungs of an animal, the method of the invention further comprises the step of subjecting the animal to extracorporeal circulatory support and oxygenation prior to providing the vascular permeability-enhancing agent. Preferably, a heart-lung machine is used according to methods known in the art. Extracorporeal circulatory support and oxygenation permits blood flow to the lungs of the animal to be minimized, thus minimizing exudation from the pulmonary blood vessels of the animal into the lungs.

Figure 3:
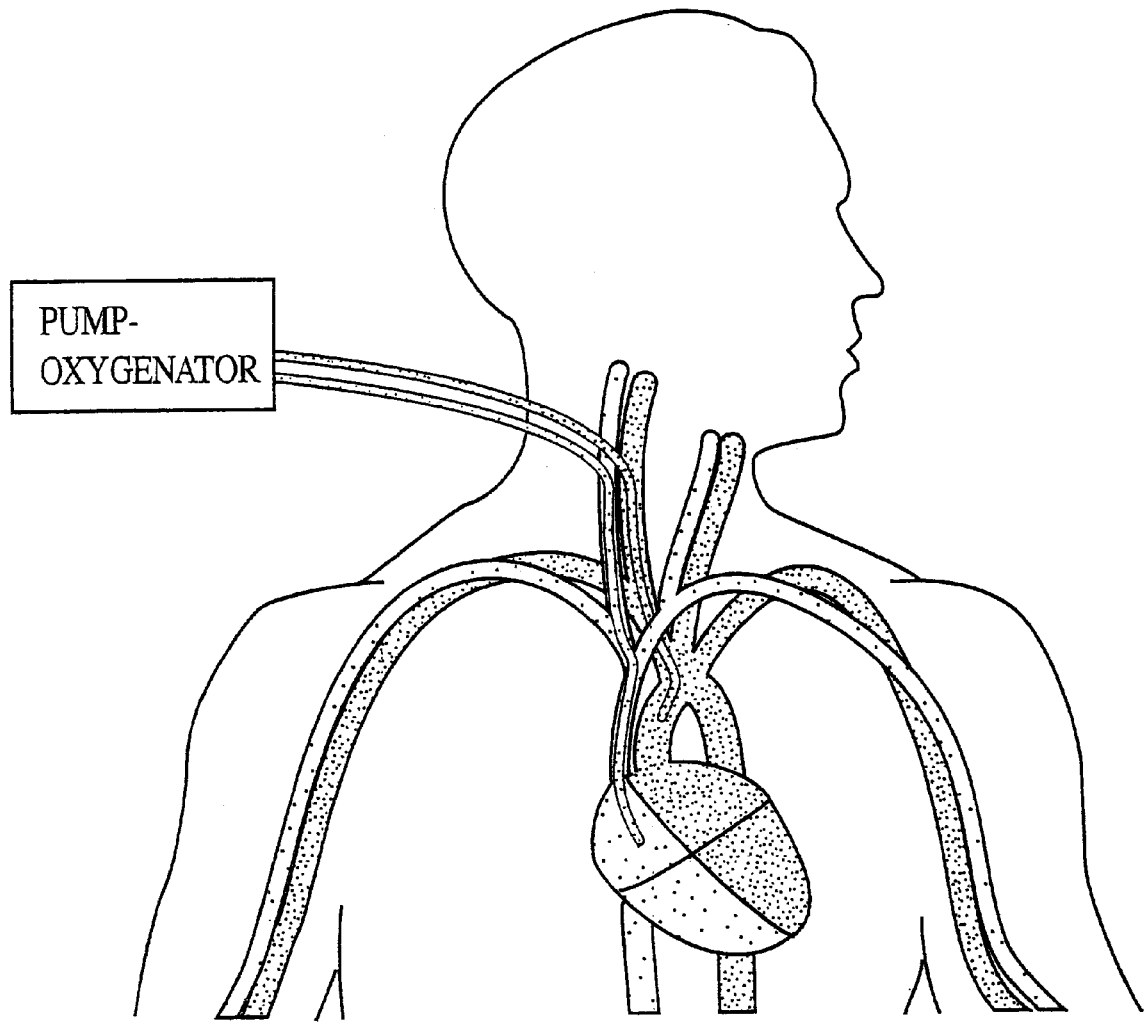
FIG. 3 is a diagram depicting the position of a pump oxygenator relative to a human patient.
Figure 4:
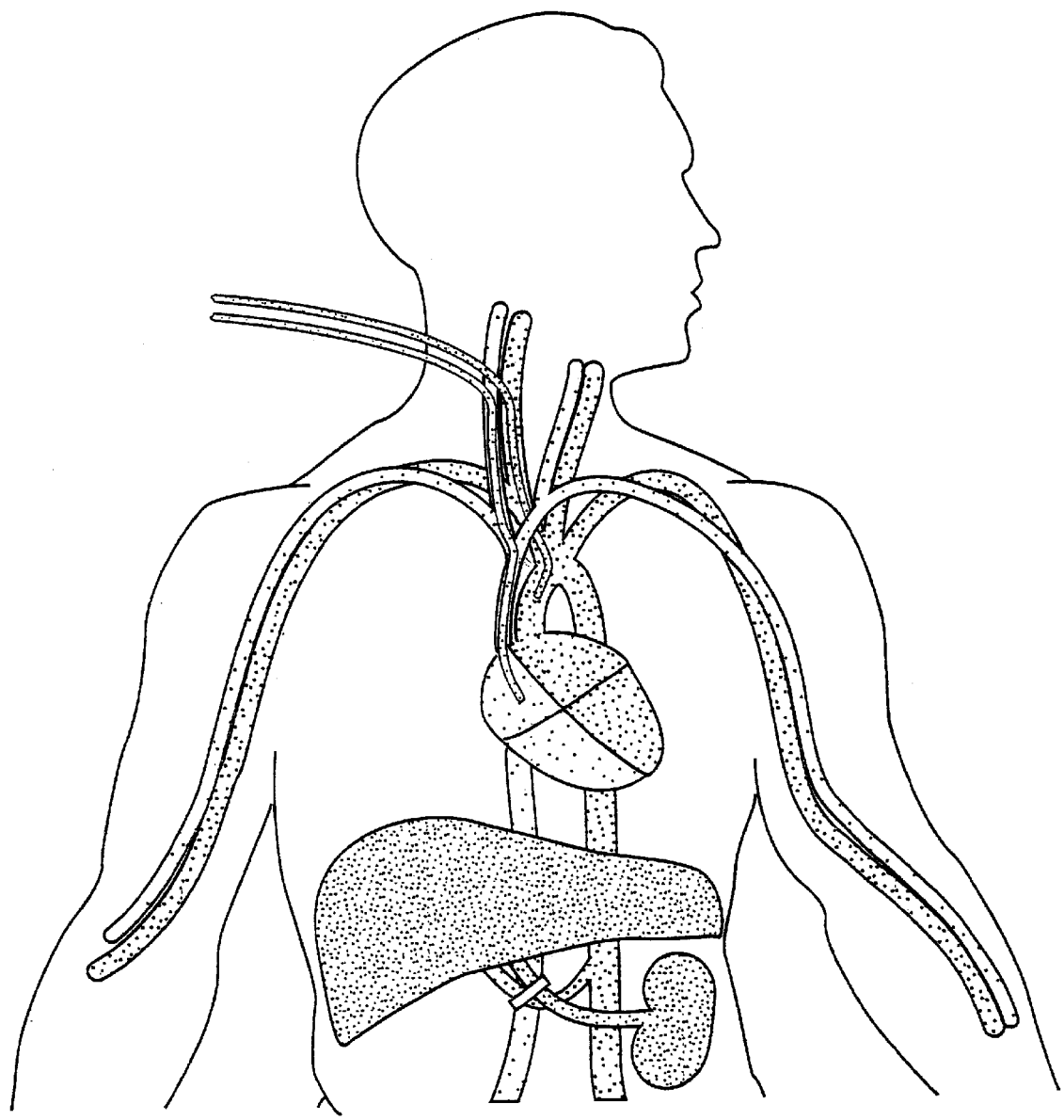
FIG. 4 is a diagram depicting the position of cannulation and a position useful for hepatic blood flow occlusion in a human patient.
Figure 5:
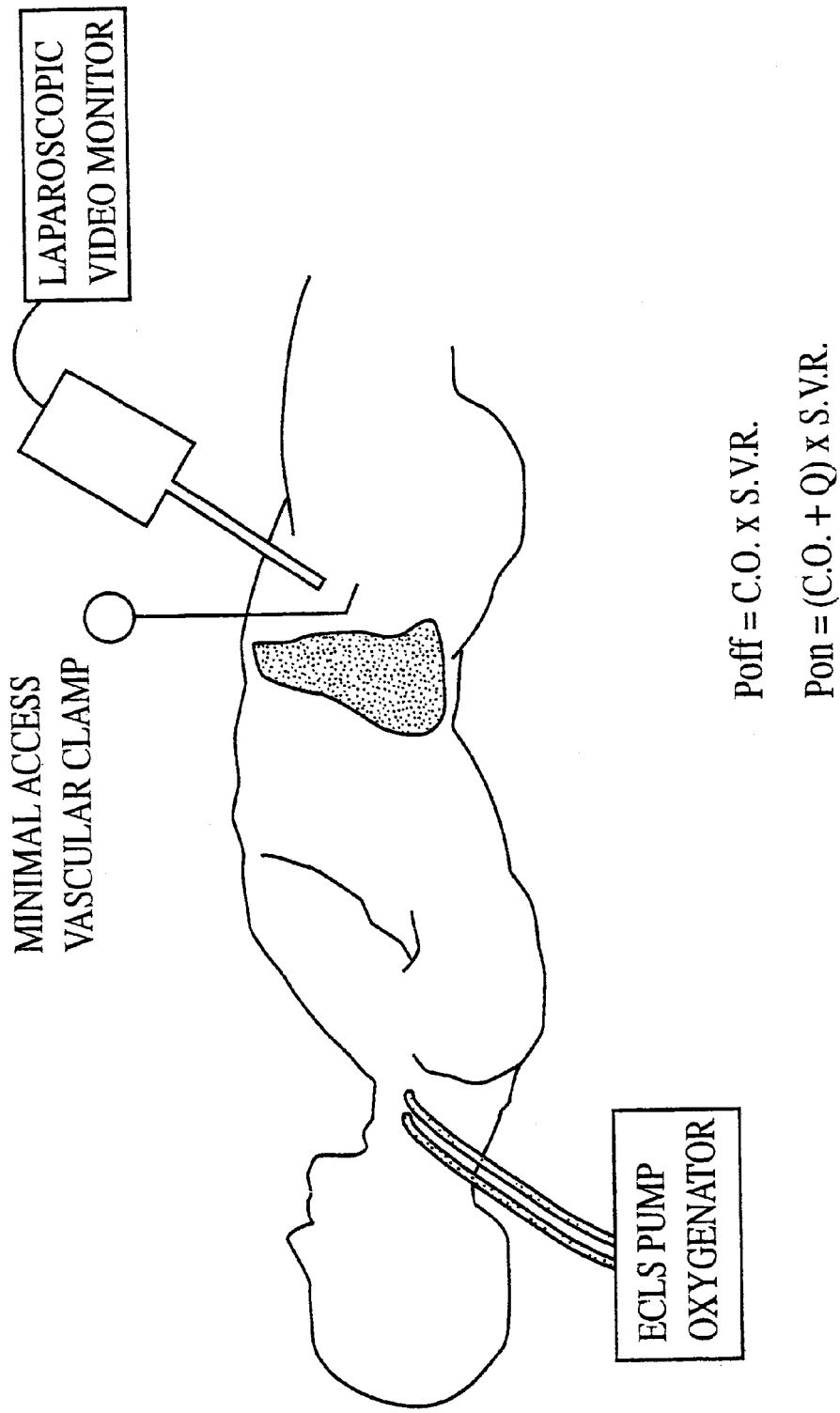
FIG. 5 is a diagram depicting the relative positions of a minimal access vascular clamp, an ECLS pump oxygenator, and a laparoscopic video monitor in a human patient.

A method of subjecting a human to extracorporeal circulatory support and oxygenation is illustrated in FIG. 5. In this method, an ECLS pump oxygenator is connected to a pair of cannulae inserted into the human as illustrated in FIG. 3, one cannula extending into the right atrium of the human, and the other cannula extending into the aorta of the human. Blood is withdrawn from the right atrium, oxygenated extracorporeally, and returned to the atrium of the human at a controlled pressure and flow rate. Using this method, blood flow to the lungs is minimized, and exudation from pulmonary blood vessels into the parenchyma of the lungs is minimized. As illustrated in FIG. 4, hepatic blood flow in the human may also be occluded.

One contemplated embodiment of the method of the invention is a method of delivering a gene vector to an extravascular tissue of an animal. The method comprises the following steps. A blood vessel associated with the tissue is isolated from the blood circulatory system of the animal. Thereafter, a vasodilating agent is provided to the vessel. Thereafter a vascular permeability-enhancing agent is provided to the vessel to increase the permeability of the endothelial layer of the vessel, the gene vector is provided to the vessel, whereby the vector is delivered to the tissue through the endothelial layer of the vessel, the perfusion pressure within the vessel is increased above the normal physiological perfusion pressure, and an oxygen-transporting agent is provided to the vessel. Thereafter a clearance solution is provided to the vessel, the clearance solution being substantially free of the vascular permeability-enhancing agent.

Thus, according to this embodiment of the method of the invention, delivery of the gene vector to the extravascular tissue is enhanced by the presence of the vasodilating agent, the presence of the vascular permeability-enhancing agent, and the increased perfusion pressure within the blood vessel of the animal. Furthermore, the gene vector and both agents remain localized in the blood vessel due to the occlusion of the vessel prior to delivery of the vector and the agents. Because an oxygen-transporting agent is provided to the vessel, the vessel may remain occluded, and the vector and agents may remain within the vessel for an extended period. Also, because a clearance solution is provided to the vessel, excess vector and agents are removed from the vessel prior to re-establishing systemic blood circulation in the animal, thereby minimizing any potential undesirable effects caused by the presence of the vector or agents in an area of the animal's body other than the vessel.

The method of the invention may be used to provide a gene vector to substantially all muscle tissues of an animal. The method comprises the following steps. The animal is subjected to extracorporeal circulatory support and oxygenation. Thereafter, a vasodilating agent is provided to the blood circulatory system of the animal, a vascular permeability-enhancing agent is provided to the blood circulatory system to increase the permeability of the endothelial layer of the vessels of the blood circulatory system, the gene vector is provided to the blood circulatory system, whereby the vector is delivered to substantially all muscle tissues through the endothelial layer of the vessels of the blood circulatory system, and the perfusion pressure within the blood circulatory system is increased above the normal physiological perfusion pressure. In order to decrease sequestration of the gene vector in the liver of the animal, the Pringle maneuver may be performed whereby hepatic blood flow to the liver is occluded. In order to decrease sequestration of the gene vector in viscera of the animal, complete visceral inflow occlusion may be performed. Complete viseral inflow occlusion may be achieved, for example, by occluding blood flow through the celiac axis, the superior mesentery artery, and the inferior mesentery artery, and may be maintained for at least fifteen minutes. These three blood vessels may be accessed, for example, by a laporoscopic or surgical procedure or by passing a balloon through the femoral artery.

The apparatus of the invention comprises an oxygenator that can be used to provide oxygen to an oxygen-transporting agent, such as the blood of an animal, prior to provision of the agent to a blood vessel of the animal. The oxygenator of the invention has a hollow body, a liquid inlet in fluid communication with the interior of the body, a liquid outlet in fluid communication with the interior of the body, a gas inlet for providing gas to the interior of a gas chamber, at least one gas-permeable membrane separating the gas chamber from the interior of the body, and a gas outlet for permitting gas to exit from the gas chamber, whereby gas exchange is enabled between a fluid in the interior of the body and a gas in the gas chamber. The oxygenator may be constructed analogously to that illustrated in FIGS. 8 and 9, wherein the gas-permeable membrane comprises PTFE tubing extending within at least a portion of the tube, and wherein the gas chamber comprises the interior of the PTFE tubing. Because of the simple construction of the oxygenator of the invention, it may be constructed inexpensively and treated as a single-use, disposable element of an extracorporeal oxygenation system. The simple construction of the oxygenator of the invention also permits it to be made with dimensions adapted to oxygenation of very small volumes of liquid, such as the volume of the contents of a blood vessel of an animal. By altering the proportions of the oxygenator, particularly the surface area of the gas-permeable membrane which is capable of contacting the liquid phase within the body of the oxygenator, the oxygenator may be made to support nearly any liquid phase flow rate. Such proportioning techniques are well known in the art.

The oxygenator of the invention is used by passing an oxygen-transporting agent through the body of the oxygenator, whereby the agent contacts the gas-permeable membrane. Oxygen, air, or another gas supplied to the gas chamber is capable of diffusing through the gas-permeable membrane and into the agent, which may be supplied to a blood vessel of an animal. As described herein, any oxygen-transporting agent may be used. An oxygenator having a relatively small volume within its hollow body may be used when the volume of agent to be supplied to an occluded blood vessel is small; similarly, an oxygenator having a proportionally greater volume may be used if the oxygenator is to be used to provide oxygen to a greater volume of agent.

Support for the hypothesis that mechanical circulatory support and extracorporeal oxygenation extends the pharmacological range of the inflammatory mediator/vasodilator mix is found in the following information. It has been found in the present invention that the isolated perfused heart survives infusion of the same histamine and papaverine doses used in skeletal muscle and these doses are tolerated as long as the mediator is flushed out before systemic circulation is restored. If these compounds gain access to the systemic circulation of an unsupported heart, cardiogenic shock ensues.

Apparatus and methods for providing a composition to a blood vessel are well known in the art and include, for example, cannulation methods, syringe-mounted hollow bore needle delivery, delivery via a length of flexible tubing engaged by a peristaltic pump, and the like.

To support the heart during administration of histamine and papaverine, two approaches may be used. First, the heart of a suitable donor may be isolated and perfused ex vivo prior to transplantation of the heart into the animal being treated. Second, the transplantation is performed first into the femoral circulation, the side branch vessels of the epigastric system are cannulated and the heart is perfused in situ, and before removing the cannula the system is flushed using a high hind limb tourniquet which prevents leaking of the pharmacological agents into the systemic circulation. Both of these procedures allow very transient use of the pharmacological agents in the superphysiologic perfusion pressures that are possible with a modified pump oxygenator without the need for any circulatory support for the rest of the animal. Therefore, the heart and lungs of the affected animal are still functioning normally.

Definitions

Certain terminology is used herein as follows.

An "extravascular tissue" is a tissue which is located in sufficient proximity to a blood vessel that exudation from the vessel under conditions of high vascular permeability is capable of contacting the tissue. By way of example, muscle tissue, being highly vascularized, is an extravascular tissue because muscle cells are located in close proximity to blood vessels, and exudate from those blood vessels is capable of contacting muscle cells.

A "vascular permeability-enhancing agent" is a composition of matter which, when supplied to a blood vessel of an animal, preferably a mammal, increases the permeability of the endothelial layer of the vessel, such that substances within the vessel may pass through the endothelial layer.

A "vasodilating agent" is a composition of matter which, when supplied to a blood vessel of an animal, preferably a mammal, increases the luminal diameter of the vessel. Stated another way, a vasodilating agent, when administered to a blood vessel of an animal, increases the caliber of the vessel.

The "perfuision pressure" within a blood vessel means the peak pressure differential between the fluid within the lumen of the vessel and the fluid surrounding the vessel. It is understood that the peak pressure within the vessel corresponds to the driving force for blood flow through the vessel by the beating action of the animal heart.

The "normal physiological" perfusion pressure within a blood vessel means the perfusion pressure within the vessel of a healthy animal in a resting state.

An "oxygen-transporting agent" means a composition of matter which, when in a liquid or solution form, is capable of capturing an oxygen molecule ($O_2$) and delivering the oxygen molecule to a biological oxygen carrier such as hemoglobin or myoglobin. By way of example, numerous synthetic blood substitutes and perfluorochemical liquids are oxygen-transporting agents.

The term "pharmaceutically-acceptable carrier" means a chemical composition with which a composition of the invention may be combined and which, following the combination, can be used to administer the composition of the invention to an animal, preferably a mammal.

A "supraphysiologic level" of a vascular permeability-enhancing agent is the level of such an agent which is present in an animal which is at rest and which is experiencing normal circulatory homeostasis.

By describing two nucleic acid sequences as "operably linked" is meant that a single-stranded or double-stranded nucleic acid moiety comprises each of the two nucleic acid sequences and that the two sequences are arranged within the nucleic acid moiety in such a manner that at least one of the two nucleic acid sequences is able to exert a physiological effect by which it is characterized upon the other.

A "macromolecular assembly" means a molecule or plurality of molecules, wherein the molecule or plurality of molecules is sufficiently large that it is not capable of passing through the endothelial layer of a blood vessel of an animal, preferably a mammal, and more preferably a human, in the absence of a supraphysiologic level of a vascular permeability-enhancing agent. By way of example, a macromolecular assembly may be a single-chain protein, a multimeric protein, a liposome, a linear nucleic acid, a virus such as an adenovirus, a picornavirus, or an adeno-associated virus, a gene vector such as a plasmid or a virus vector, or the like. Also by way of example, the macromolecular assembly may be an adenovirus vector comprising a human minidystrophin gene, as described (Ragot et al., 1993, Nature 361:647–650). Further by way of example, the macromolecular assembly may be an adenovirus vector comprising plasmid pAdDeltaRSV, modified in that the plasmid comprises a full length dystrophin cDNA (Koening et al., 1988, Cell 53:219–228), wherein the pAdDelta RSV plasmid comprises a pBSA-2 vector backbone comprising an RSV promoter operably linked to the dystrophin cDNA, the promoter-cDNA sequence being flanked by adenoviral 5'- and 3'-ITR sequences.

A "gene vector" means a composition of matter which comprises a nucleic acid and which is capable of delivering that nucleic acid to an animal cell when the gene vector is contacted with the animal cell. By way of example, a gene vector may be a virus which is capable of infecting a human muscle cell and which comprises a nucleic acid encoding the human dystrophin protein operably linked to a promoter/regulatory sequence, whereby when the virus contacts a human muscle cell, the nucleic acid is provided to the cell, and the cell is capable of expressing the protein.

A "promoter/regulatory sequence" means a DNA sequence which is required for expression of a gene operably linked to the promoter/regulatory sequence. In some instances, this sequence may be the core promoter sequence and in other instances, this sequence may also include an enhancer sequence and other regulatory elements which are required for expression of the gene in a tissue-specific manner.

"Extracorporeal circulatory support" means a mechanical device which is capable of circulating the blood of an animal through all or a part of the circulatory system of the animal without assistance from the heart of the animal. By way of example, a heart-lung machine, which is well known in the art, is a device which is useful for providing extracorporeal circulatory support.

"Venorrhaphy" means surgical repair of a vein, for example by suturing an incision in the vein in such a way as to retain patency of the vein without hemorrhage While the invention is described with reference to the following examples, these examples are provided for the purposes of illustration only, and the invention should in no way be construed as being limited to these examples, but rather, should be construed to encompass any and all variations which become evident as a result of the teaching provided herein.

EXAMPLE 1

Convectional Transport of Adenovirus Across the Microvascular Barrier Promotes Systemic Gene Transfer Data which supports the hypothesis that transient hepatic inflow occlusion minimizes unwanted viral sequestration are now presented. The experimental Pringle maneuver was performed on rats which were administered recombinant adenovirus into the central circulation. This resulted in greatly reduced hepatic staining intensity relative to control animals on which the Pringle maneuver was not performed. The methods used in the experiments presented in this Example are now described.

Construction and amplification of the E1, E3 deleted recombinant adenovirus vector designated AdCMVlacZ has been described (Kozarsky et al., 1993, Som. Cell Molec. Genet. 5:449–458). Recombinant adenovirus was administered to rats using a total dose of approximately $10^9$ particles per gram of rat body weight. A frozen aliquot of the virus stock, which comprised 10% (v/v) glycerol, was thawed and diluted 1:5 in PBS immediately prior to infusion, yielding a titer of $10^{12}$ particles per milliliter. Animals were anesthetized by forelimb intramuscular injection of 75 milligrams per kilogram body weight of ketamine and 5 milligrams per kilogram body weight of xylazine. C57Bl10 mice and Fisher 355 rats were used.

The experiments presented in this Example were designed to investigate differences in convectional transport of a suspension of adenovirus from the lumen of vascular capillaries to the interstitium of muscle tissue, which differences resulted from alterations in the age of the animal used, the method of providing the suspension to the animal, the composition of the suspension, or a combination of these factors. Approximately $5\times10^{10}$ AdCMVlacZ particles per gram of body weight were administered to all animals in these experiments. Owing to the outflow resistance of the micropipettes and microcannulae used to administer AdCMVlacZ in these experiments, it is understood that applied infusion pressures are always much higher than the pressures achieved in the vascular beds. Consistency was maintained by using regulated pressures to drive fluid flow through these devices. Tissue specimens obtained from the animals used in these experiments were whole mount stained for p-galactosidase activity as described (Sanes et al., 1986, EMBO J. 5:3133–3142) following perfusion-fixation with 0.2% (v/v) glutaraldehyde and 2% (v/v) paraformaldehyde in PBS at necropsy. The results of these experiments are summarized in Table 1.

AdCMVlacZ was administered to each of the newborn rats of series A of Table 1 by injecting the virus vector into the retro-orbital vein of the rat using the tip of a glass micropipette, wherein virus vector suspension flow was driven by a picopump under foot pedal control.

AdCMVlacZ was administered to each of the newborn rats of series B of Table 1 by injecting the virus vector into the common femoral artery of the rat using the tip of a glass micropipette, wherein virus vector suspension flow was driven by a picopump under foot pedal control.

AdCMVlacZ was administered to each of the 2 week-old rats of series C of Table 1 immediately following laparotomy and placement of an occlusive vascular clamp across the hepatic inflow vessels. The virus vector was injected into the femoral vein, and the clamp was left in place for 30 minutes before being released.

The 2 week-old rats of series D of Table 1 were intended to serve as control animals relative to the animals of series C. The rats of series D were injected with the same amount of virus vector as those of series C, but hepatic inflow occlusion was not performed on the rats of series D.

The adult rats of series E of Table I underwent femoral artery and vein isolation and a 3-0 prolene tourniquet was placed at the level of the proximal thigh. Heparin at 100 units per kilogram of body weight was intravenously administered to the blood circulatory system of the each rat, and the femoral artery or each was cannulated using a heat-tapered polyethylene tube (PE 10, Becton Dickinson, Sparks, Md.), the lumen of which was in fluid communication with the lumen of a 30 gauge needle mounted at the end of the tube not inserted into the artery. Following tightening of the tourniquet, microvascular clamps were placed to occlude blood flow through the femoral vessels. Infusion of AdCMVlacZ suspension and a 1 milliliter "chase" volume of PBS through the tube and into the artery was driven by a regulated pressure supply, which provided the virus vector suspension continuously at 20 pounds per square inch gauge pressure. The clamps and tourniquet were left in place from five to forty-five minutes, after which time they were removed and arteriotomy was repaired using 11-0 suture (Sharpoint, Reading, Pa.). The small groin incision was closed using a resorbable suture.

The adult rats of series F in Table 1 were treated the same as the rats of series E, except that the regulated pressure supply provided the virus vector suspension continuously at 80 pounds per square inch gauge pressure.

The mice of series G of Table 1 underwent femoral artery injection, as described for the rats of series B, except that a proximal thigh tourniquet and clamps occluding blood flow through the femoral artery were applied prior to delivery of the virus vector. A 100 microliter aliquot of the virus vector was provided using a glass micropipette, followed by a 1 milliliter aliquot of saline. The aliquots were permitted dwell in the artery for five minutes.

The mice of series H of Table 1 were treated the same as the mice of series G, except that 100 microliters of a solution which comprised either 10 millimolar histamine or 0.3 milligram per milliliter papaverine was provided to the artery immediately prior to infusion of the virus vector.

The mice of series I of Table 1 were treated the same as the mice of series H, except that both histamine and papaverine was administered to each mouse.

The mice of series J of Table 1 were treated the same as the mice of series I, except that venorrhaphy was performed on each mouse immediately prior to release of the tourniquet.

The rats of series K of Table 1 underwent femoral artery and vein isolation, and a 3-0 prolene tourniquet was placed at the level of the proximal thigh. Hindlimb circulation was primed by infusing into the artery a composition comprising either 150 micrograms of papaverine in 500 microliters of PBS at pH 7.4 or 500 microliters of 10 millimolar histamine in PBS at pH 7.4. Five minutes later, $6 \times 10^{10}$ AdCMVlacZ particles suspended in 500 microliters of the composition were infused into the artery, followed by a 1 milliliter chase volume of PBS driven from a reservoir maintained at 80 pounds per square inch gauge. The clamps and tourniquet remained in place for a total of forty-five minutes following which the limb circulation was flushed with 3 milliliters of PBS.

The rats of series L of Table 1 were treated the same as the rats of series K, except that the composition comprised both histamine and papaverine, at the concentrations indicated.

In each of the rats of series M of Table 1, limb perfusion was performed as in the rats of series K, except that two overlapping tourniquets were placed to allow complete isolation with transmuscular placement of two overlapping tourniquets as well as vascular access via the superficial inferior epigastric vessel. This required advancement of a second catheter across a venous valve at the junction of this side branch with the greater saphenous vein. Furthermore, the composition comprised both histamine and papaverine at the concentrations indicated, and venorrhaphy was performed on each rat immediately prior to release of the tourniquets.

Newborn mice pups were anesthetized after feeding to ensure a stomach filled with milk, for the purpose of providing optical contrast. The skin of an individual mouse was incised over the abdominal wall and was reflected laterally to provide access to the rectus abdominus muscle in the distribution of the superior epigastric artery. Through a dissecting microscope at approximately 100× magnification, single erythrocytes were readily visualized as they coursed single-file through the skeletal muscle capillaries. Histamine, papaverine, or both, dissolved in PBS, were applied topically to the capillaries. Video recordings were made against a timeline with an attached camera. Similar observations were made in the adult mouse and the adult rat of perfusion in the distal portion of the adductor muscles as they overlie the proximal tibia, again to optimize optical contrast in a thin muscle.

The results of the experiments presented in Example 1 are now described.

A novel system for the study of microvascular dynamics has been used to assess the ability of recombinant human adenovirus vector AdCMVlacZ (which has a Stoke's radius of approximately 70 nanometers; Stewart et al. 1993, EMBO J. 12:2589–2599) to cross the endothelial barrier of mammalian blood vessels in vivo. Several interventions having synergistic effects on microvascular permeability have been identified, and a strategy for efficient gene transfer to the majority of muscle fibers in the adult rat hindlimb has been developed. Given the similarity among mammalian muscle tissues, it is clear that the present system can be used analogously in any mammal, and perhaps even any animal.

Among gene transfer vectors considered for therapeutic use, recombinant adenoviruses are notable for extraordinarily efficient local gene transfer following intramuscular injection in newborn mice (Quantin et al., 1992, Proc. Natl. Acad. Sci. 89: 2581–2584; Acsadi et al., 1994, Hum. Molec. Genet. 33: 579–584). Adenovirus vectors have been used to transduce gene expression in murine models for several human diseases (Kozarsky et al., 1996, Nature Genet. 13: 54–62; Ragot et al., 1993, Nature 361: 647–650). The muscle mass of the newborn mouse hindlimb comprises approximately 30 milligrams of tissue. Diffusion of adenovirus vector for several millimeters through the immature extracellular matrix of newborn mouse muscle tissue enables transduction of most of the nascent muscle fibers. However, the limitations of focal delivery become apparent in older mice and rats, in which gene transduction effected by intramuscular injection of an adenovirus vector becomes progressively less efficient and remains localized to a volume of several cubic millimeters around the site of injection (Acsadi, 1994, supra).

Adenovirus vector delivery via the intravenous route offers access primarily to the liver, where a discontinuous endothelium is thought to facilitate gene transfer from the vascular space to the parenchymal cell mass (Kozarsky, 1996, supra; Kozarsky et al., 1994, J. Biol. Chem. 268: 13695–13702).

The shortcomings of adenovirus vector delivery via direct injection or intravascular delivery may be overcome by developing adenovirus vector delivery methods which are useful for transepithelial delivery, where possible (e.g. Raper et al., 1996, Pancreas 12: 401–410).

Adenovirus vector transport across the continuous endothelial barrier of skeletal muscle can be described as the sum of three delivery components: convective, diffusive, and vesicular exchange delivery (Weinbaum et al., 1995, Symp. Soc. Exp. Biol. 49:323–345). The classical studies of Starling (1896, J. Physiol. 19:312), Krogh (1919, J. Physiol. 52: 409), and Pappenheimer et al. (1951, Am. J. Physiol. 167:13–28) provide relevant data from experiments with skeletal muscle in which transport rates for solutes of different molecular dimensions and lipid solubilities were quantified.

The behavior of larger macromolecules was more recently quantified, giving rise to the two-pore theory of transvascular exchange, wherein only one in thirty thousand pores are large enough to admit particles up to a quarter the diameter of the adenovirus (Rippe et al., 1994, Physiol. Rev. 74:163–219). As predicted by extrapolation from these data, recombinant adenovirus administered intravascularly gains minimal access to skeletal muscle fibers, as confirmed by the staining of muscle fiber depicted in FIG. 1a. Intravascular delivery of adenovirus vector was not significantly improved by applying supraphysiologic perfusion pressures simultaneously with vector administration to increase Starling forces in favor of transudation, as indicated by the staining pattern depicted in FIG. 1b and by the data presented in Table 1. These results indicate that the vascular epithelium has remarkable integrity and implies that the rates of vesicular and convectional transport of virus vector to muscle tissue from the interstitium is inconsequential. These results also suggest that intravascular delivery of an adenovirus vector is an inefficient systemic gene transfer strategy.

TABLE 1

EXPERIMENTS ON ADENOVIRUS UPTAKE BY MICROVASCULATURE, LIVER, AND MUSCLE FIBERS FOLLOWING CIRCULATORY DELIVERY

| Series | Species | Age | Infusion Site Devices Used | Infusate | Pressure | n | Xgal Pattern |
|---|---|---|---|---|---|---|---|
| A | Rat | N | IV, Microppt | None | Low | 3 | V+, L++ |
| B | Rat | N | Femoral artery, Microppt | None | Mod | 3 | V+, L++ |
| C | Rat | 2w | IV, Hepatic inflow occlusion | None | Low | 2 | V+, L+ |
| D | Rat | 2w | IV, Microppt | None | Low | 2 | V+, L++ |
| E | Rat | A | Femoral Artery, Cath, Tqt #1 | H | Mod | 3 | V++, L+ (FIG. 1a) |
| F | Rat | A | Femoral Artery, Cath, Tqt #1 | None | High | 3 | V++, L+ (FIG 1b) |
| G | Mouse | A | Femoral artery Microppt, Tqt #1 | None | Mod | 3 | V+, L++ |
| H | Mouse | A | Femoral artery Microppt, Tqt #1 | H or P | Mod | 2 | V++, L+ |
| I | Mouse | A | Femoral artery Microppt, Tqt #1 | H + P | Mod | 3 | Lethal |
| J | Mouse | A | Femoral artery Microppt, Tqt #1 | H + P | Mod, D | 1 | V+, L+, M+ |
| K | Rat | A | Epigastric artery, Cath, Tqt #1 | H or P | Mod | 3 | V+, L+, M+ |
| L | Rat | A | Epigastric artery, Cath, Tqt #1 | H + P | High | 1 | Lethal |
| M | Rat | A | Epigastric artery, Cath, Tqt #2 | H + P | High, D. | 9 | M+++ (FIG. 2) |

Abbreviations used: N: neonate; 2w: two weeks; A: adult; IV: intravenous; Tql: Tourniquet, Tqt #2: modified (transmuscular) tourniquet; Microppt: glass micropipette; Cath: plastic catheter; D: venous drainage; H: histamine; P: papaverine; V: vascular; L: liver; M: muscle; +: weakly present; ++: strongly present; Low: 5 psig (Pounds per square inch gauge); Mod: 20 psig; High 80 psig.

An alternative approach was investigated, based upon the pathophysiology of inflammation in skeletal muscle, which can be reproduced by topical application of histamine or another vascular permeability-enhancing agent. There is ultrastructural evidence for the transient appearance of gaps between adjacent endothelial cells following application of such an agent to endothelial tissue, the gaps having a width on the order of 1 micrometer. Moreover, electron micrographs document the ability of colloidal HgS particles up to 35 nanometers in diameter and of larger chylomicrons to traverse these intercellular gaps. (Majno et al., 1961, supra).

It was hypothesized that an induced process of inflammatory exudation, would promote vector delivery from the circulation to adult skeletal muscle in vivo by enhancing convectional transport of the vector across the vascular epithelium. The systemic side effects of vasoactive mediator infusions were avoided through the application of an isolated limb perfusion system. As indicated by the data presented in Table 1, the synergistic effects of histamine, papaverine (a potent endothelium-independent vasodilating agent; Wennmalm, 1994, J. Int. Med. 235:317–327), and application of supraphysiologic perfusion pressure resulted in highly efficient gene transfer from the vascular space to the muscle fibers en masse.

The homogeneity of gene transduction in response to these manipulations is depicted in FIG. 2 where Xgal staining of the majority of the muscle fibers in the adult rat hindlimb is visible at several levels of magnification. Although retention of particles smaller than the adenovirus vector at the capillary basal lamina has been documented by electron microscopy (Majno et al., 1961, supra), the results described herein indicate that this barrier has been traversed.

The composite intervention using histamine, papaverine, and supraphysiologic perfusion pressure was lethal if the circulatory isolation of the limb to which the intervention was directed was incomplete. However, animals in which circulatory isolation of the limb was adequate tolerated the procedure well and returned to normal ambulation.

These results presented in this Example indicate that delivery of an adenoviral vector in conjunction with providing a vascular permeability-enhancing agent, a vasodilating agent, and supraphysiologic perfusion pressure is efficient and well tolerated by mammals. This method of adenovirus vector delivery achieves an efficiency and volume of vector distribution which is essential for gene therapy in numerous genetic diseases such as muscular dystrophy.

The histological appearance of two adjacent muscles of the quadriceps, as depicted in FIG. 2, Panel B, demonstrates the absence of artifactual staining in nonperfused tissued. In FIG. 2, Panel B, blood supply to the rectus femoris was occluded using a tourniquet. The results describe herein also establish the existence of an epimysial tissue barrier to adenovirus diffusion, as depicted in FIG. 2, Panels A and B.

In the experiments presented in this Example, a dramatic reduction in gene delivery to the limb vasculature was also noted, as indicated in FIG. 2, Panels C and D. This observation suggests that the endothelial cells of the muscle tissue vasculature either lost the ability to take up virus as a transient side effect of the mediator infusion or were effectively bypassed by the convectional flow of fluid into the interstitium. This observation further suggests that the method of the invention can be used to deliver an adenovirus vector specifically to an extravascular tissue, without significant uptake of the vector by the endothelial cells of the blood vessel(s) supplying that tissue.

Microvascular perfusion as viewed in real time through a dissecting microscope was initially used to evaluate several pharmacologic agents. Topical application of 10 millimolar histamine rapidly induced vasodilation, and was followed within seconds by progressive capillary stasis. Topical application of 300 micrograms per milliliter papaverine resulted in capillary recruitment and increased local perfusion. Topical application of both agents resulted in sustained perfusion of capillaries, and there was evidence of local edema formation. These findings suggest that the synergistic effects of these mediators on vector delivery relate to the ability of papaverine to overcome the autoregulatory or edema-induced closure of precapillary resistance vessels. The acute toxicity of the mediators noted during inadequate hindlimb isolation relates to their hemodynamic side effects (Thom et al., 1995, J. Clin. Oncol. 13:264–273).

The hemodynamic side effects of the mediators complicates their use in the central circulation during attempted systemic gene delivery (see, e.g., Eyre, 1970, J. Pharm. Pharmacol. 22:104–109; Silverman et al., 1988, J. Appl. Physiol. 64:210–217). Furthermore, concurrent use of adrenergic agonists to support the circulation may reverse the desired effects on gene delivery and/or result in myocardial damage, especially in the setting of cardiomyopathy.

Using the blood vessel occlusion techniques described herein, or other such techniques known in the art, the side effects resulting from systemic delivery of the mediators may be minimized or avoided. In addition, these side effects could theoretically be overcome by the institution of extracorporeal circulatory support prior to the systemic infusion of mediators. In this context, rapid clearance of circulating virus vector by the liver could emerge as a secondary problem. However, the data provided in Table 1 regarding the reduction of hepatic virus uptake by hepatic inflow occlusion suggests that a minimally invasive surgical procedure, such as a laparoscopic procedure, could largely overcome this problem.

The proposed combination of surgical and pharmacological approaches described in this Example represents a general method for systemic gene delivery. The clinical significance of the method is dependent upon how well the procedure is tolerated in larger animals than those used in this Example. This issue is described further in Example 3 herein.

EXAMPLE 2
Additional Compounds Useful for Enhancing Microvascular Permeability Compounds which may also function to enhance microvascular permeability in addition to histamine and papaverine, include, but are not limited to, platelet activating factor, serotonin, bradykinin and nitroprusside. Capillary permeability induced following administration of these compounds may be assessed by quantifying the uptake of fluorescently labeled 70- to 100-nanometer-diameter dextran particles.

Given the data which has been described, the invention may be extended as follows.

Systemic gene transfer may be accomplished in large animals, including humans using a combination of inflammatory and vasodilatory agents provided extracorporeal support is in place.

Provision of adequate circulatory support and oxygenation depends directly on the implications of allometric scaling, i.e., the mathematical relationship which governs the organ function of animals of different size. Each muscle cell or fiber in the murine heart and diaphragm works about 10–15 times the rate of the human heart and diaphragm. Thus, a heart-lung bypass circuit for small rodents must transport oxygen and blood at 10–15 times the rate needed in humans. The fluid dynamic resistance, as determined by Poiseuille's law, becomes rate limiting because of the wall thickness of the cannulae.

Straightforward solutions to the problem are to perform the experiments in large enough animals to model the flow rates achievable in humans and to use the paradigms of pediatric and adult cardiovascular and critical care management. The cannulation sites in the animal will dictate the flow rate. The carotid and jugular approach will be preferentially used because of its minimally invasive nature and because of the fact that it has been used successfully for years even in pediatric extracorporeal membrane oxygenation (ECMO). If necessary, the aortocaval cannulation may be used as it is used in open heart surgery. The types of cannulation and positions of the pump, etc., are illustrated in FIGS. 3, 4 and 5.

It is important to determine whether inflammatory mediators alter the immune response to neoantigen expression. In addition, it is important to determine the relationship between the level of gene transfer achieved and the magnitude of the physiological disturbance resulting from the initial intervention. In the case of muscular dystrophy, it is known that there is a threshold effect of gene dosage and if it is not possible to achieve this dose, then it is not likely that the procedure will be beneficial. It is possible to compensate for gene transfer inefficiency and enhance the gene therapy effect by using stronger promoter sequences to drive gene expression. Tissue specific expression may also be possible using tissue specific promoter sequences.

It is anticipated that a patient in need of the procedure described herein would undergo general endotracheal intubation anesthesia, would undergo a neck incision as is currently used for extracorporeal membrane oxygenation, and would undergo placement of laparoscopic ports for timely performance of a Pringle maneuver. The flow through the ECMO circuit would commence followed by infusion of vasodilator, then virus and then inflammatory mediator, with flow rates and additional volume used as needed to achieve a hyperdynamic circulation. After completion of a short period of exudation which may be of the order of as little as five minutes, blood would be cleansed of the residual inflammatory mediator to promote rapid weaning from ECMO. This would be accomplished through the use of a cell saver, one or more hemofiltration or hemodialysis units connected in series, or other recovery device. The patient would then be progressively weaned from extracorporeal oxygenation. In the animal models studied thus far, treated animals are ambulatory within a short period following surgery.

EXAMPLE 3
Extracorporeal Circulatory Support and Blood Oxygenation in Sheep

The experiments described in this Example were performed to confirm that the circulatory system of an animal larger than a mouse or a rat can be supported extracorporeally under the conditions described herein for delivery of a macromolecular assembly such as an adenovirus vector. Sheep were subjected to cardiopulmonary bypass, and were then administered either 3.75 or 7.5 milligrams per kilogram body weight of papaverine and either 25 micrograms per kilogram body weight or 125 milligrams per kilogram body weight of histamine. Relevant physiological characteristics of the sheep were monitored in real time.

The materials and methods used in the experiments presented in this Example are now described.
Surgical Procedure The extracorporeal circulation support system described herein was designed to permit the animal to tolerate massive fluid exudation under the influence of histamine and papaverine.

Healthy sheep were orally administered a Nichol's prep which consisted of one gram of erythromycin and one gram of neomycin base the night before surgery to minimize intestinal dilatation with air. The sheep were fasted overnight (i.e. at least twelve hours) with ab libitum access to water. The animals, after constraint using a squeeze cage, were sedated by intramuscular administration of 10 milligrams per kilogram body weight of ketamine and induced for anesthesia using intravenous bolus doses of 30 milligrams per kilogram of pentobarbital. The vocal cords of each were sprayed with 2% (v/v) lidocaine, after which the animals were endotracheally intubated and connected to a mechanical ventilator. Tidal volume was set at 15 milliliters per kilogram body weight with a respiratory rate of 20 per minute. The animals were weighed to update records. Anesthesia was started using 3% (v/v) isoflurane and was maintained using 1–2% (v/v) isoflurane.

The depth of anesthesia was determined by lightly pinching the animal's tail at fifteen minute intervals throughout the procedure. If any antalgic response was noted the animal was given additional anesthetic by doubling the percentage isoflurane for five minutes and then reverting to the original percentage only when the antalgic response to tail pinch ceased.

Each animal was positioned in dorsal recumbency and electrocardiogram leads were placed on the extremities. All animals underwent cannulation as described herein. In addition to access for cardiopulmonary bypass, the cannula was used, after euthanasia, for saline perfusion of the animal to replace plasma in the vascular space. In all cases the animals were euthanized after the experimental pump run following barbiturate overdose by disconnecting the ventilator for ten minutes immediately prior to saline perfusion.

The peritoneal cavity was entered through a right subcostal incision and the hepatoduodenal ligament was identified and mobilized. A Rammel tourniquet was placed in position to ultimately occlude the portal vein and hepatic artery, but the clamp was left in the open position. The fascial edges of the abdominal incision were then loosely approximated with towel clips.

A small vertical incision was made over the palpable left carotid pulse and deepened just far enough to allow placement of an arterial catheter for pressure monitoring purposes. A longitudinal incision was then made over the pulse of the right common carotid artery. This incision was deepened to enable full exposure of the right external jugular vein and common carotid artery. A 29-inch wire-wrapped venous cannula was placed in the right external jugular vein and carefully advanced inferiorly until its tip assumed a position estimated to be in the right atrium, wherein the estimate was based on surface landmarks and on the distance the catheter was advanced. Next, a 14-inch wire wrapped canula was placed in the right common carotid artery. In both 55cases, vascular cannulation presupposed the achievement of proximal and distal control. The carotid canula was advanced until its tip assumed a position estimated to be in the aortic root, near the aortic valve.

The left external jugular vein was cannulated with a cordis port, following which a Swan-Ganz catheter was advanced until its tip was in the pulmonary artery. The appropriate ports of the Swan-Ganz were then attached to pressure transducers to allow simultaneous monitoring of pulmonary artery pressure and central venous pressure.

The right groin was then incised longitudinally over the palpable pulse of the right common femoral artery, and a 14 French wire-wrapped canula was inserted between the proximal and distal control points and advanced against arterial flow retrograde to the point where its tip was in the right common iliac artery.

Once all cannulae were secured into position, they were attached to the circuit of a pump oxygenator primed with a solution which comprised 120 millimolar sodium chloride, 5 millimolar potassium chloride, 3 millimolar magnesium chloride, 24 millimolar sodium bicarbonate, and which was bubbled with a carbogen mixture, comprising 5% (v/v) carbon dioxide and 95%(v/v) oxygen, until a pH of 7.4 was achieved. Throughout the remainder of the experiment, the carbogen mixture was allowed to flow through the bubble oxygenator at an empirically determined rate high enough to ensure a carbon dioxide partial pressure of 40 torr. This served to fix the arterial pH at approximately 7.4 throughout the entire length of the pump run.

One hundred cubic centimeters of blood was drawn into a pair of sixty cubic centimeter syringes, each containing sixty units of heparin. The heparinized blood was quickly centrifuged to separate red blood cells from plasma. The plasma was then mixed with a filtered solution of Evans blue dye in PBS, approximately 0.5 grams of plasma in 5 milliliters of PBS. Hepatic inflow occlusion was achieved by tightening the Rammel tourniquet previously placed around the hepato-duodenal ligament. After one minute of swirling to gently mix the Evans blue dye with the plasma, the plasma was remixed with the separated red blood cells and the entire solution was returned to the animal's blood stream by way of the central venous cordis through the left external jugular vein. Completion of the infusion of the Evans blue dye defined time point t=−1 minute. At t=0 minutes, bypass was begun at a pump rate of 3 liters per minute. At t=2 minutes, the animal was infused with a bolus of 150 milligrams of papaverine in 5 milliliters of vehicle by way of the distal-most port on the arterial line leaving the pump oxygenator unit. It was anticipated that this potent NO-independent vasodilator would bring about an immediate drop in the blood pressure of the animal. Over the ensuing two minutes, the animal's blood pressure was normalized by increasing the flow rate through the pump and infusing an additional volume of the same solution used to prime the pump. At t=4 minutes, a bolus of histamine comprising 25 micrograms per kilogram per kilogram was infused intra-arterially through the point most distal from the pump of the arterial line of the pump oxygenator.

After a thirty-minute pump run, the pump was stopped for two minutes to assess the contractility of the heart and to measure the pulmonary-arterial, central venous, and aortic pressures in the absence of extra-corporeal circulation. As soon as these values were obtained, the animal was humanely euthanized with a massive overdose of barbiturate.

The configuration of the pump oxygenator was altered to permit infusion of a 140 millimolar sodium chloride solution adjusted to pH 7.4 using 10 millimolar Tris hydrochloric acid by way of the arterial cannulae. Immediately prior to exsanguination, the Rammel tourniquet occluding hepatic inflow was released. The venous cannulae was attached to a separate roller pump to allow complete exsanguination of the euthanized animal into an appropriate receptacle. The animal was exsanguinated using 10 liters of the sodium chloride solution. Following exsanguination, incisions were made to permit access to the following organs to obtain tissue specimens: heart, lung, liver, kidney, small and large intestine, brain, testicle, and the following skeletal muscles: diaphragm, left and right biceps and triceps from the thoracic extremity, left quadriceps, biceps femorus, gastrocnemious soleus, extensor digitorum longus from the pelvic extremity, iliopsoas, and posterior body wall muscle at point of maximal compression by animal's body weight against the operating table. The last muscle specimen listed served to establish the variability introduced by the pressure points in positioning the animal on the operating table.

Each tissue sample was immediately placed in an aluminum foil-wrapped, 50 cubic centimeter conical centrifuge tube having an identifying label. The individual specimens were weighed and a fragment comprising approximately 2 grams of tissue was removed for mincing and for formamide extraction. Evans Blue Dye content was quantitated spectrophotometrically and was normalized to tissue wet and dry weights.

The results of the experiments presented in this Example are now described.

Figure 6A:
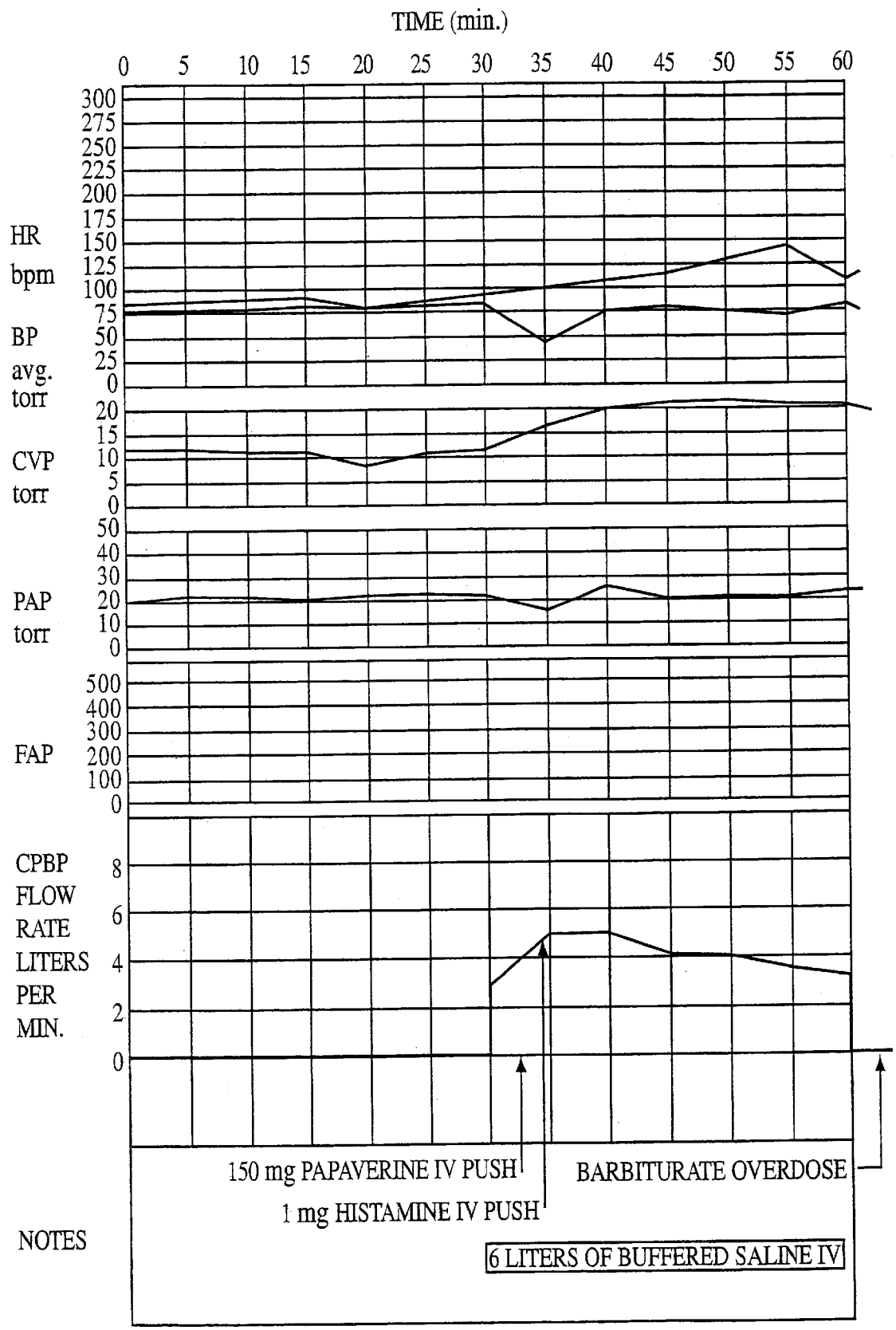
FIG. 6a is a graph which summarizes physiological data obtained from an approximately 40 kilogram sheep to which 150 milligrams of papaverine and 1 milligram of histamine were administered. HR means heart rate in beats per minute. BP means average blood pressure measured in torr. CVP means central venous pressure measured in torr. PAP means pulmonary arterial pressure measured in torr. FAP means femoral arterial pressure measured in torr. CPBP means cardiopulmonary by-pass unit flow rate in liters per minute.
Figure 6B:
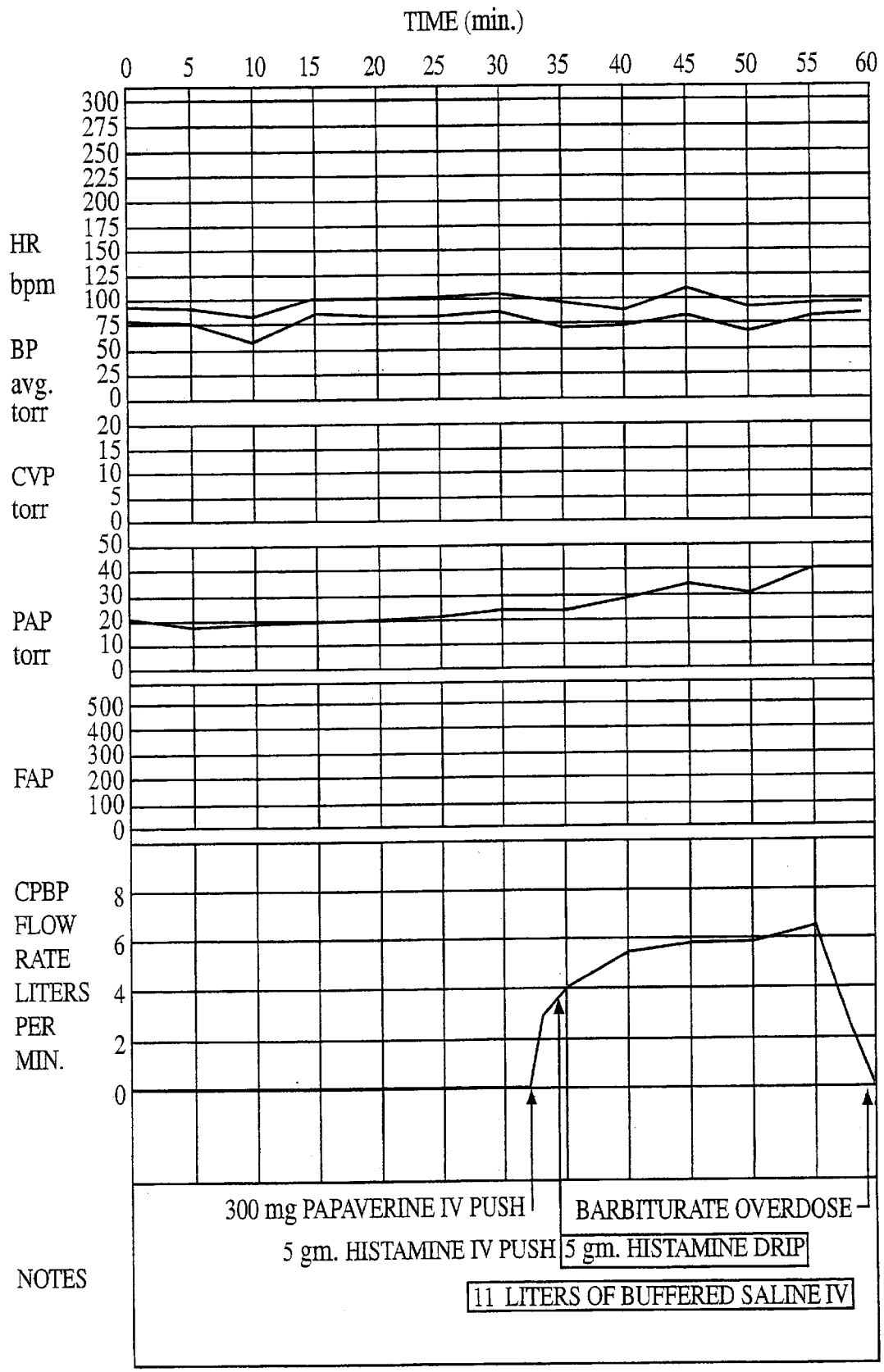
Figure 7:
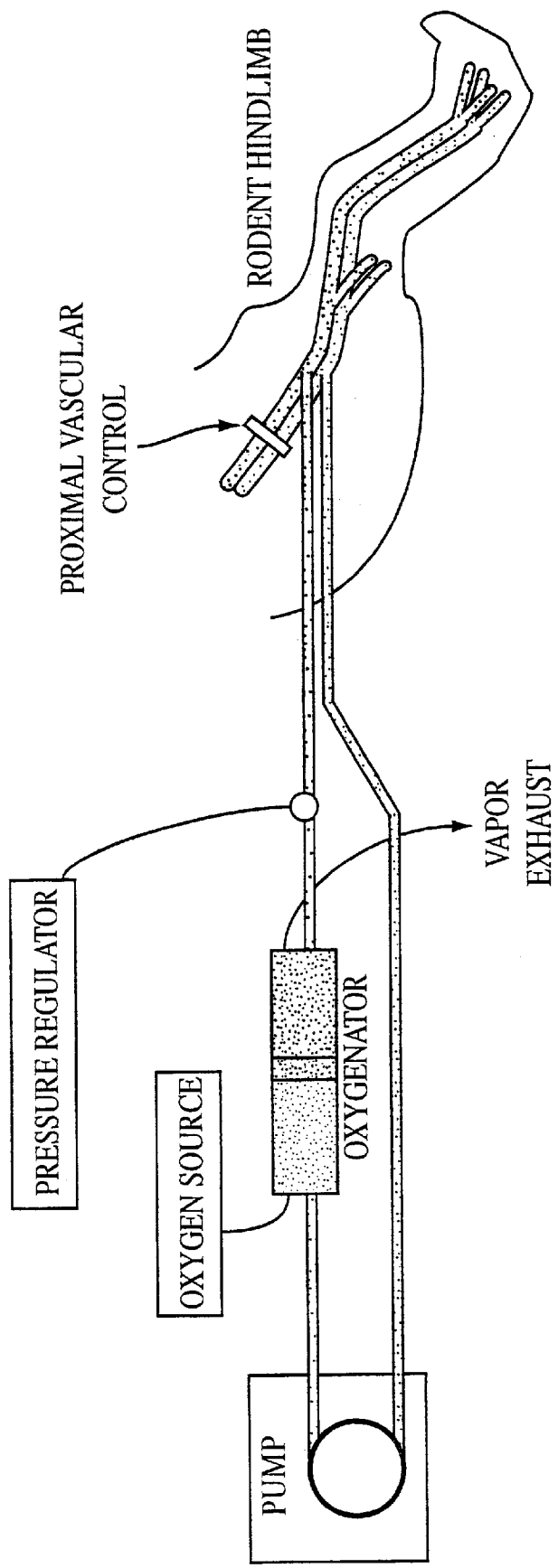
FIG. 7 is a diagram which illustrates the use of a pump, oxygenator, and pressure regulator to deliver a gene vector to an occluded rodent hindlimb. The system operates as follows. An artery and a vein in the rodent's hindlimb are isolated from the rodent's blood circulatory system using a tourniquet or the like. The gene vector is introduced into the artery. A venous catheter connects the vein to the inlet of a pump. The pump passes blood withdrawn from the vein through an oxygenator and into the artery through a second catheter. A pressure regulator maintains a constant perfuision pressure in the artery of the rodent.

The experiments presented in this Example have been performed using two sheep, and the results of those experiments are summarized in FIGS. 6a and 6b.

One 40 kilogram sheep was intravenously administered 150 milligrams of papaverine and 1 milligram of histamine, and physiological data recorded using this sheep are depicted in FIG. 6a. As expected, the blood pressure of the sheep dropped following administration of the vasodilating agent, papaverine, and the vascular permeability-enhancing agent, histamine. However, as depicted in FIG. 6a, the extracorporeal circulatory support system was able to stabilize the hemodynamic state of the sheep to the extent that, from approximately ten minutes after administration of the compounds, the sheep's blood pressure was approximately equal to the blood pressure prior to administration. As noted in the figure, the extracorporeal circulatory support system supplied 6 liters of PBS to the sheep, suggesting that approximately 6 liters of fluid had been exuded from the vascular system of the sheep to extravascular tissues.

A second 40 kilogram sheep was intravenously administered 300 milligrams of papaverine and 5 grams of histamine, and physiological data recorded using this sheep are depicted in FIG. 6b. As expected, the blood pressure of the sheep dropped following administration of the vasodilating agent, papaverine, and the vascular permeability-enhancing agent, histamine. However, as depicted in FIG. 6b, the extracorporeal circulatory support system was able to stabilize the hemodynamic state of the sheep to the extent that, from at least twenty-five minutes after administration of the compounds, the sheep's blood pressure was approximately equal to the blood pressure prior to administration. As noted in the figure, the extracorporeal circulatory support system supplied 11 liters of PBS to the sheep, suggesting that approximately 11 liters of fluid had been exuded from the vascular system of the sheep to extravascular tissues.

These results confirm that the extracorporeal circulatory support system described herein is capable of stabilizing the hemodynamic state of an animal under the conditions described herein for delivery of a macromolecular assembly such as an adenovirus vector.

Experiments in rats indicated that distribution of Evan's blue dye complexed with albumin is predictive of tissue infectivity by recombinant marker adenoviruses delivered by way of the bloodstream. Following intravascular administration of AdCMVlacZ and Xgal staining, blue color was detectable throughout the liver, but was undetectable in skeletal muscle. When Even's blue, results were similar, with an estimated quantitative ratio greater than 1000:1 distribution between liver and skeletal muscle. It was discovered that performance of the Pringle maneuver decreased this ratio to about 200:1 (liver:skeltal muscle) without increasing uptake by skeletal muscle. This ratio was approximately 6:1 in the sheep to which 150 milligrams of papaverine and 1 milligram of histamine were administered and was approximately 2:1 in the sheep to which 300 milligrams of papaverine and 5 grams of histamine were administered. These data are strongly predictive of widespread global transfer of adenovirus vector to skeletal muscle by way of the vascular space in animals.

EXAMPLE 4

Transfer of a Human Mini-Dystrophin Gene to Rat Muscle Tissue and Expression Therein.

The adenovirus vector designated AdCMVΔ17–48 dys was constructed as follows. A plasmid comprising the Sal I linkered Δexon 17–48 mini-dystrophin cDNA cloned into pUC18, as described (Acsadie et al., 1991, Nature 352:815–819) was obtained. The plasmid pAdCMVlacZ as described (Kozarsky et al., 1994, J. Biol. Chem. 268:13695–13702), was also obtained. pAdCMVlacZ is a shuttle plasmid comprising map units 0–1 and 9–16 of human adenovirus 5 flanking a cytomegalovirus (CMV)-based transcriptional cassette which drives constitutive expression of the *E. coli* lacZ gene. pAdCMVlacZ was cleaved at a Xho I endonuclease site and the cDNA from the plasmid comprising the cDNA was subcloned in the sense orientation with respect to the CMV promoter of pAdCMVlacZ as a Sal I restriction fragment to yield a plasmid designated pADCMVMini-1.

AdCMVΔ17–48dys was made by linearizing plasmid pADCMVMini-1 with the unique-site-cutting endonuclease Pvu I and was co transfected with a Cla I-restricted adenoviral genome d1327 into 293 cells, as described (Graham et al., 1977, J. Gen. Virol. 36:59–74). Plaques resulting from growing recombinant viruses were isolated and expanded as described (Graham et al., 1991, In: Methods in Molecular Biology, Murray, ed., Humana, Clifton, N.J., 109–128). Lysates from the plaque expansions were used to infect 293 cells which were subsequently collected and subjected to immunofluorescent staining with the primary antibody, NCL-Dys-2 (Novocastra Laboratories, Newcastle upon Tyne, UK). Recombinant viruses that stained positive for the presence of dystrophin in 293 cells were subjected to Western blot analysis, and viruses expressing a mini-dystrophin protein of the expected size were selected for amplification. Following three rounds of purification, the virus stocks were expanded, and adenovirus preparations were generated using standard methods. 293 cells were infected at a multiplicity of infection of about 100 particles per cell, and the transduced cells were analyzed by immunofluorescence and Western blot. These preparations were used in place of AdCMVlacZ in perfusion of rat hindlimbs, as described for the rats of Series M in Example 1 herein.

Figure 1B:
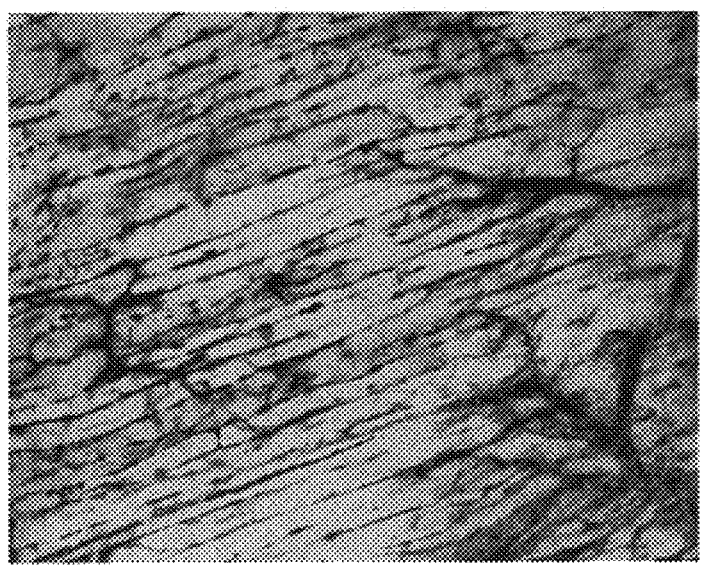
Figure 1C:
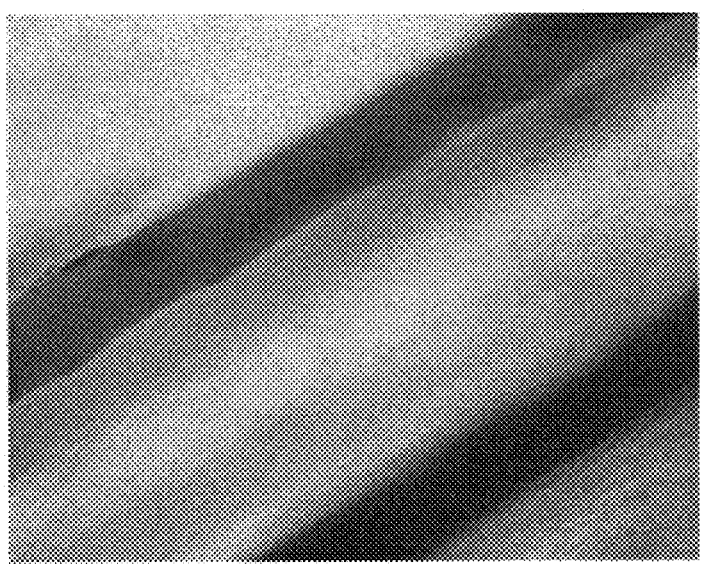
Figure 11A:
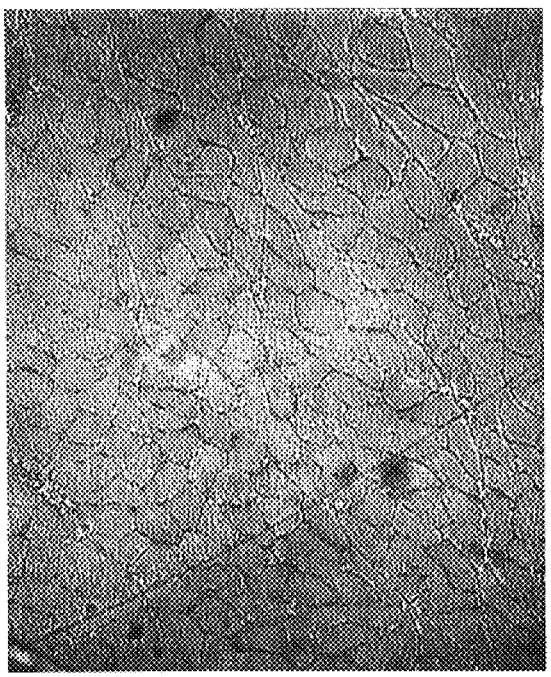
FIG. 11a is an image which depicts a cross-section of a rat gastrocnemius muscle to which the adenovirus vector, AdCMVΔ17–48dys, was delivered and which was immunofluorescently stained using NCL-Dys-2, which is a fluorescently-labeled antibody which specifically binds to an epitope which is present in human dystrophin but which is not present in rat dystrophin.
Figure 11B:
FIG. 11b is an image which depicts a cross-section of a rat gastrocnemius muscle to which the adenovirus vector, AdCMVlacZ, was delivered and which was immunofluorescently stained using NCL-Dys-2.

Cryosections of gastrocnemius muscle obtained from rats one week after perfusion with AdCMVΔ17–48dys were immunofluorescently stained with NCL-Dys-2, which specifically binds to an epitope of human dystrophin, but which does not bind to rat dystrophin. As depicted in FIG. 1a, the vector was delivered to cells of the rat gastrocnemius, and the mini-dystrophin protein encoded by AdCMVΔ17–48dys was expressed in those cells. Moreover, the staining pattern is identical to that expected for endogenous dystrophin production in the rat cells. Rat gastrocnemius cells to which no virus vector was delivered and rat gastrocnemius cells to which the vector AdCMVlacZ were delivered (as depicted in FIG. 11b) exhibited no immunofluorescent staining using NCL-Dys-2.

The results presented in this Example demonstrate that the compositions and methods described herein are useful for intravascular delivery of a gene vector to mammalian muscle cells and that such muscle cells are able to express a gene delivered thereby.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for delivering a macromolecular assembly having a diameter not greater than about 1 micrometer to an extravascular tissue of an animal, the composition comprising the macromolecular assembly and a vascular permeability-enhancing agent, wherein the vascular permeability-enhancing agent is not conjugated with a macromolecule.

2. The composition of claim 1, wherein the macromolecular assembly is a gene vector.

3. The composition of claim 1, wherein the vascular permeability-enhancing agent is selected from the group consisting of histamine, acetylcholine, an adenosine nucleotide, arachidonic acid, bradykinin, cyanide, endothelin, endotoxin, interleukin-2, ionophore A23187, nitroprusside, a leukotriene, an oxygen radical, phospholipase, platelet activating factor, protamine, serotonin, tumor necrosis factor, vascular endothelial growth factor, a venom, and a vasoactive amine.

4. The composition of claim 3, wherein the vascular permeability-enhancing agent is selected from the group consisting of histamine and vascular endothelial growth factor.

5. The composition of claim 1, further comprising a vasodilating agent.

6. The composition of claim 5, wherein the vasodilating agent is selected from the group consisting of papaverine, nimodipine, hydralazine, nitric oxide, epoprostenol, tolazoline, arninone, milrinone, nitroglycerine, isosorbide dinitrate, isosorbide mononitrate, and an organic nitrate compound.

7. The composition of claim 6, wherein the vasodilating agent is papaverine.

8. The composition of claim 1, further comprising an oxygen-transporting agent.

9. A kit for providing a macromolecular assembly to an extravascular tissue of an animal, the kit comprising a vascular permeability-enhancing agent and a vasodilating agent, wherein the vascular permeability-enhancing agent is not conjugated with a macromolecule.

10. The kit of claim 9, further comprising the macromolecular assembly.

11. The kit of claim 10, wherein the macromolecular assembly is a gene vector comprising a human gene selected from the group consisting of a gene encoding dystrophin, a gene encoding utrophin, a gene encoding a sarcoglycan, and a gene encoding a minidystrophin.

12. The kit of claim 9, further comprising an oxygen-transporting agent.

13. The kit of claim 9, further comprising at least one disposable element of an extracorporeal circulatory support and oxygenation system.

14. The kit of claim 13, wherein the at least one disposable element is an oxygenator having a hollow body, a liquid inlet in fluid communication with the interior of the body, a liquid outlet in fluid communication with the interior of the body, a gas inlet for providing gas to the interior of a gas chamber, at least one gas-permeable membrane separating the gas chamber from the interior of the body, and a gas outlet for permitting gas to exit from the gas chamber, whereby gas exchange is enabled between a fluid in the interior of the body and a gas in the gas chamber.

15. The kit of claim 14, wherein the body is a tube, wherein the gas-permeable membrane comprises PTFE tubing extending within at least a portion of the tube, and wherein the gas chamber comprises the interior of the PTFE tubing.

16. A method of delivering a macromolecular assembly to an extravascular tissue of an animal, the method comprising
providing a vascular permeability-enhancing agent to a blood vessel associated with the extravascular tissue to increase the permeability of the endothelial layer of the vessel, wherein the vascular permeability-enhancing agent is not conjugated with a macromolecule, and
providing the macromolecular assembly to the vessel, whereby the assembly is delivered to the extravascular tissue through the endothelial layer of the vessel.

17. The method of claim 16, wherein the macromolecular assembly is a gene vector.

18. The method of claim 17, further comprising providing a vasodilating agent to the vessel.

19. The method of claim 16, wherein the tissue is muscle tissue.

20. The method of claim 19, wherein the muscle tissue is striated muscle tissue.

21. The method of claim 17, wherein the gene vector is an adenoviral gene vector.

22. The method of claim 16, wherein the macromolecular assembly is a gene vector comprising a human gene.

23. The method of claim 22, wherein the human gene is selected from the group consisting of a gene encoding human dystrophin, a gene encoding utrophin, a gene encoding a sarcoglycan, and a gene encoding a minidystrophin.

24. The method of claim 23, wherein the gene vector comprises a promoter/regulatory region operably linked to the human gene, wherein the promoter/regulatory region is selected from the group consisting of a human skeletal muscle creatine phosphokinase promoter/regulatory region, a murine skeletal muscle creatine phosphokinase promoter/regulatory region, a promoter/regulatory region of a gene which is ordinarily expressed in a human skeletal muscle cell, and a human constitutive promoter region.

25. The method of claim 16, further comprising increasing the perfusion pressure within the vessel above the normal physiological perfusion pressure after providing the macromolecular assembly to the vessel.

26. The method of claim 16, further comprising isolating the vessel from the blood circulatory system of the animal prior to providing the macromolecular assembly to the vessel.

27. The method of claim 26, wherein the vessel is isolated from the blood circulatory system of the animal prior to providing the vascular permeability-enhancing agent to the vessel.

28. The method of claim 26, further comprising providing a clearance solution to the vessel after providing the macromolecular assembly to the vessel, the clearance solution being substantially free of the vascular permeability-enhancing agent.

29. The method of claim 16, further comprising providing an oxygen-transporting agent to the vessel after isolating the vessel from the blood circulatory system.

30. The method of claim 16, further comprising subjecting the animal to extracorporeal circulatory support and oxygenation prior to providing the vascular permeability-enhancing agent.

31. The method of claim 16, further comprising occluding the blood supply to the liver of the animal prior to providing the macromolecular assembly.

32. The method of claim 16, wherein the animal is a human.

33. A method of delivering a gene vector to an extravascular tissue of an animal, the method comprising
  a) isolating a blood vessel associated with the tissue from the blood circulatory system of the animal; thereafter
  b) providing a vasodilating agent to the vessel; thereafter
  c) providing a vascular permeability-enhancing agent to the vessel to increase the permeability of the endothelial layer of the vessel;
    providing the gene vector to the vessel, whereby the vector is delivered to the extravascular tissue through the endothelial layer of the vessel;
    increasing the perfusion pressure within the vessel above the normal physiological perfusion pressure; and
    providing an oxygen-transporting agent to the vessel; and thereafter
  d) providing a clearance solution to the vessel, the clearance solution being substantially free of the vascular permeability-enhancing agent.

34. A method of providing a gene vector to substantially all muscle tissues of an animal, the method comprising
  a) subjecting the animal to extracorporeal circulatory support and oxygenation; and thereafter
  b) providing a vasodilating agent to the blood circulatory system of the animal;
    providing a vascular permeability-enhancing agent to the blood circulatory system to increase the permeability of the endothelial layer of the vessels of the blood circulatory system;
    providing the gene vector to the blood circulatory system, whereby the vector is delivered to substantially all muscle tissues through the endothelial layer of the vessels of the blood circulatory system; and
    increasing the perfusion pressure within the vessel above the normal physiological perfusion pressure.

35. The composition of claim 1, wherein the macromolecular assembly has a diameter not greater than about 100 nanometers.

36. The composition of claim 1, wherein the macromolecular assembly has a diameter not greater than about 90 nanometers.

37. The composition of claim 1, wherein the macromolecular assembly has a diameter not less than about 7 nanometers.

38. The composition of claim 1, wherein the macromolecular assembly has a diameter not less than about 35 nanometers.

39. The composition of claim 1, wherein the macromolecular assembly has a diameter not less than about 70 nanometers.

40. The method of claim 16, wherein the macromolecular assembly has a diameter not greater than about 100 nanometers.

41. The method of claim 16, wherein the macromolecular assembly has a diameter not greater than about 90 nanometers.

42. The method of claim 16, wherein the macromolecular assembly has a diameter not less than about 7 nanometers.

43. The method of claim 16, wherein the macromolecular assembly has a diameter not less than about 35 nanometers.

44. The method of claim 16, wherein the macromolecular assembly has a diameter not less than about 70 nanometers.

* * * * *